US012559735B2

(12) United States Patent
Rosenberg

(10) Patent No.: US 12,559,735 B2
(45) Date of Patent: Feb. 24, 2026

(54) DEVICE FOR DETECTING ORGANOPHOSPHATES

(71) Applicant: PlantVax, Inc., Rockville, MD (US)

(72) Inventor: Yvonne J. Rosenberg, Washington, DC (US)

(73) Assignee: PlantVax, Inc., Rockville, MD (US)

( * ) Notice: Subject to any disclaimer, the term of this patent is extended or adjusted under 35 U.S.C. 154(b) by 970 days.

(21) Appl. No.: 17/609,376

(22) PCT Filed: May 6, 2020

(86) PCT No.: PCT/US2020/031682
§ 371 (c)(1),
(2) Date: Nov. 6, 2021

(87) PCT Pub. No.: WO2020/227413
PCT Pub. Date: Nov. 12, 2020

(65) Prior Publication Data
US 2022/0062906 A1     Mar. 3, 2022

Related U.S. Application Data

(60) Provisional application No. 62/844,440, filed on May 7, 2019.

(51) Int. Cl.
*C12N 9/18* (2006.01)
*C12N 9/02* (2006.01)
*C12N 9/80* (2006.01)

(52) U.S. Cl.
CPC ............. *C12N 9/18* (2013.01); *C12N 9/0071* (2013.01); *C12N 9/80* (2013.01); *C12Y 114/14001* (2013.01); *C12Y 301/01001* (2013.01); *C12Y 305/01005* (2013.01)

(58) Field of Classification Search
None
See application file for complete search history.

(56) References Cited

U.S. PATENT DOCUMENTS

| | | | | |
|---|---|---|---|---|
| 2005/0089926 A1* | 4/2005 | Taylor | ..................... | C12N 9/18 435/7.1 |
| 2015/0167047 A1* | 6/2015 | Smith | ..................... | A61L 2/28 435/31 |
| 2016/0251703 A1 | 9/2016 | Gilboa-Geffen et al. | | |
| 2016/0262657 A1 | 9/2016 | Ahmad et al. | | |

OTHER PUBLICATIONS

International Preliminary Report of Patentability and Written Opinion dated Nov. 18, 2021 and received in PCT/US2020/031682.
International Search Report and Written Opinion dated Jul. 31, 2020 and received in PCT/US20/31682.
Foreign Office Action received in corresponding Brazilian Application dated Jan. 28, 2025.

* cited by examiner

*Primary Examiner* — Erin M. Bowers
(74) *Attorney, Agent, or Firm* — Michele M. Wales; InHouse Patent Counsel

(57) ABSTRACT
This invention relates to a device that can be used is used to detect organophosphates and carbamate on surfaces including food, clothing (including as wearable pesticide detectors) and machinery.

25 Claims, 11 Drawing Sheets
Specification includes a Sequence Listing.

Figure 1D
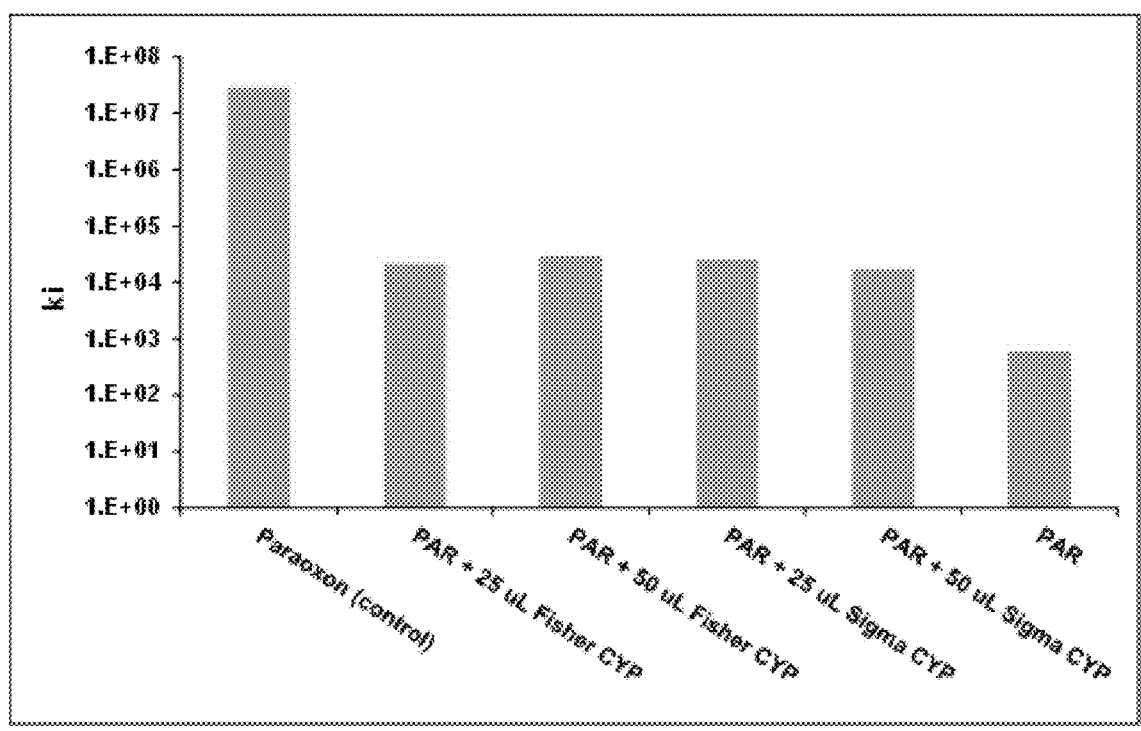
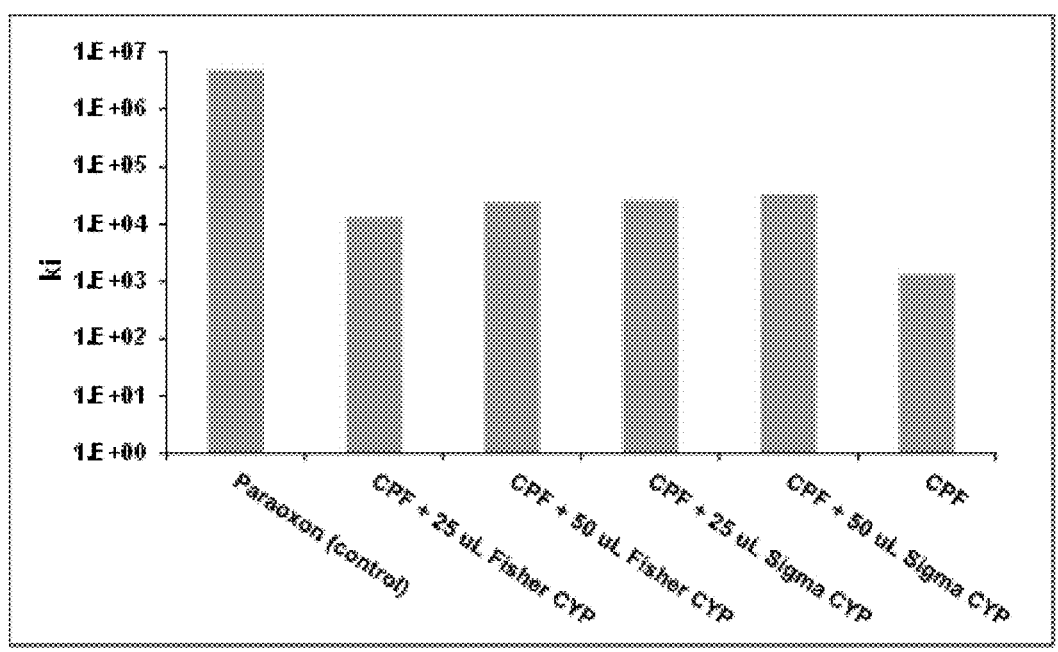

Figure 2. Sequences of primate ChEs.

SEQ #1 human AChE E4-E6 isoform

```
MRPPQCLLHTPSLASPLLLLLLWLLGGGVGAEGREDAELLVTVRGGRLRGIRLKTPG
GPVSAFLGIPFAEPPMGPRRFLPPEPKQPWSGVVNATTFQSVCYQYVDTLYPGFEGT
EMWNPNRELSEDCLYLNVWTPYPRPTSPTPVLVWIYGGGFYSGASSLDVYDGRFLVQ
AERTVLVSMNYRVGAFGFLALPGSREAPGNVGLLDQRLALQWVQENVAAFGGDPTSV
TLFGESAGAASVGMHLLSPPSRGLFHRAVLQSGAPNGPWATVGMGEARRRATQLAHL
VGCPPGGTGGNDTELVACLRTRPAQVLVNHEWHVLPQESVFRFSFVPVVDGDFLSDT
PEALINAGDFHGLQVLVGVVKDEGSYFLVYGAPGFSKDNESLISRAEFLAGVRVGVP
QVSDLAAEAVVLHYTDWLHPEDPARLREALSDVVGDHNVVCPVAQLAGRLAAQGARV
YAYVFEHRASTLSWPLWMGVPHGYEIEFIFGIPLDPSRNYTAEEKIFAQRLMRYWAN
FARTGDPNEPRDPKAPQWPPYTAGAQQYVSLDLRPLEVRRGLRAQACAFWNRFLPKL
LNATDTLDEAERQWKAEFHRWSSYMVHWKNQFDHYSKQDRCSDL
```

SEQ #2 Macaca AChE

```
MLLLSRACATSMWIPFTLVSRELRCGTLTESCLRIACTLMCGPRPTSPTPVLVWIYG
GGFYSGASSLDVYDGRFLVQAERTVLVSMNYRVGAFGFLALPGSREAPGNVGLLDQR
LALQWVQENVAAFGGDPTSVTLFGESAGAASVGMHLLSPPSRGLFHRAVLQSGAPNG
PWATVGMGEARRRATQLAHLVGCPPGGTGGNDTELVACLRTRPAQVLVNNEWHVLPQ
ESVFRFSFVPVVDGDFLSDTPEALINAGDFHGLQVLVGVVKDEGSYFLVYGAPGFSK
DNESLISRAEFLAGVRVGVPQVSDLAAEAVVLHYTDWLHPEDPARLREALSDVVGDH
NVVCPVAQLAGRLAAQGARVYAYVFEHRASTLSWPLWMGVPHGYEIEFIFGIPLDPS
RNYTTEEKIFAQRLMRYWANFARTGDPNEPRDPKAPQWPPYTAGAQQYVSLDLRPLE
VRRGLRAQACAFWNRFLPKLLSATDTLDEAERQWKAEFHRWSSYMVHWKNQFDHYSK
QDRCSDL
```

SEQ #3 HuBChE wild type

```
MHSKVTIICIRFLFWFLLLCMLIGKSHTEDDIIIATKNGKVRGMNLTVFGGTVTAFL
GIPYAQPPLGRLRFKKPQSLTKWSDIWNATKYANSCCQNIDQSFPGFHGSEMWNPNT
DLSEDCLYLNVWIPAPKPKNATVLIWIYGGGFQTGTSSLHVYDGKFLARVERVIVVS
MNYRVGALGFLALPGNPEAPGNMGLFDQQLALQWVQKNIAAFGGNPKSVTLFGESAG
AASVSLHLLSPGSHSLFTRAILQSGSFNAPWAVTSLYEARNRTLNLAKLTGCSRENE
TEIIKCLRNKDPQEILLNEAFVVPYGTPLSVNFGPTVDGDFLTDMPDILLELGQFKK
TQILVGVNKDEGTAFLVYGAPGFSKDNNSIITRKEFQEGLKIFFPGVSEFGKESILF
HYTDWVDDQRPENYREALGDVVGDYNFICPALEFTKKFSEWGNNAFFYYFEHRSSKL
PWPEWMGVMHGYEIEFVFGLPLERRDNYTKAEEILSRSIVKRWANFAKYGNPNETQN
NSTSWPVFKSTEQKYLTLNTESTRIMTKLRAQQCRFWTSFFPKVLEMTGNIDEAEWE
WKAGFHRWNNYMMDWKNQFNDYTSKKESCVGL
```

Figure 2 - Continued

SEQ#4 MaBChE wild type

GI:290795732

MDSKVTIICIRLLFWFLLLCMLIGKSHTEDDIVIATKNGKVRGMNLTVLGGTVTAFLGIPYAQP
PLGRLRFKKPQSLTKWSDIWNATKYANSCYQNIDQSFPGFHGSEMWNPNTDLSEDCLYLNVWIP
APKPKNATVMIWIYGGGFQTGTSSLHVYDGKFLARVERVIVVSMNYRVGALGFLALPGNPEAPG
NMGLFDQQLALQWVQKNIAAFGGNPKSVTLFGESAGAASVSLHLLSPGSHSLFTRAILQSGSSN
APWAVTSLYEARNRTLTLAKLTGCSRDNETEIVKCLRNKDPHEILLNEAFVVPYGTLLSVNFGP
TMDGDFLTEMPDILLELGQFKKTQILVGVNKDEGTAFLVYGAPGFSKDNDSIITRNEFQEGLKI
FFPGVSEFGKESILFHYTDWVDDQRPENYREALDDVVGDYNIICPALEFTKKFSEWGNNAFFYY
FEHRSSKLPWPEWMGVMHGYEIEFVFGLPLERRVNYTKAEEILSRSIVKRWANFAKYGNPNGTH
NNSTKWPVFKSTEQKYLTLNTESSRILTKLRAQQCRFWTSFFPKVLEMTGNIDEAEWEWKAGFH
RWSNYMMDWKNQFNDYTSKKESCVGL

100

110

120

130

140

SCALE 2 : 1

DEVICE FOR DETECTING ORGANOPHOSPHATES

CROSS-REFERENCE TO RELATED APPLICATIONS

This application is a § 371 National Stage Application of PCT/US20/31682 filed on May 6, 2020, which claims priority to U.S. 62/844,440 filed on May 7, 2019, both of which are hereby incorporated by reference in their entirety.

The invention was made with Government support under NIH grant No. 1R43ES029405. The Government may have certain rights to the invention

FIELD OF THE INVENTION

This invention relates to a device that can be used to detect organophosphate (OP) and carbamates (C) compounds, on surfaces including food, clothing (including as wearable pesticide detectors), environmental samples and machinery.

DESCRIPTION OF THE RELATED ART

Worldwide, the routine use of pesticides including organophosphates to control agricultural, household and structural pests has reached greater than 5 billion tons annually, which potentially exposes greater than 1.8 billion civilians and tons of agricultural produce. In the USA, levels are high enough to result in 10,000-20,000 pesticide poisonings among just the ~2 million agricultural workers annually. While pesticides greatly increase food production by reducing insect infestations, they are toxic compounds and have environmental and health effects. WHO Class I and Class II OP and carbamate pesticides constitute a diverse group of chemical structures, but all potentially exhibit a common mechanism of toxicity similar to nerve agents, that is, active site modification of acetylcholinesterase (AChE) resulting in its inhibition, accumulation of acetylcholine, over-stimulation of cholinergic receptors, and consequent clinical signs of cholinergic toxicity.

Although safe for humans and other mammals at the low doses used, there is a growing concern about the effects of long-term exposure to these chemicals by farm workers and the level of pesticide consumed with food. This is especially true in Asia. At high exposures, acute toxicity can occur leading to seizures, brain damage and cognitive and behavioral defects and often death by respiratory failure. In addition to occupational exposure to prolonged or high pesticide, OP and carbamate doses, their potency has been associated with a major cause of disability and death. In this context, insecticide poisoning is often the preferred method of suicide in Asia, killing more than 100,000 people annually in India alone. In addition, pesticide use has been associated with the neurocognitive deficits and neuroendocrine alterations described in veterans as Gulf War syndrome and more recently, it is thought that pesticides were used by Islamist terrorists to attack schools In Afghanistan from 2010-2013 injuring over 2,000 girls.

The neurotoxicity caused by spraying of insecticides may result from dermal or inhalation exposure from the particles in the air, on clothing or machinery or orally from the residue on food. In the latter context, the effect on children appears to happen at lower levels than for adult exposure. These health consequences, particularly associated with the use of OP and carbamate ("C") insecticides, could be reduced by monitoring produce and eliminating the consumption of OP-contaminated food. See, e.g., www.who.int/ipcs/publications/pesticides_hazard_2009.pdf. In the US, the level of pesticide residue allowed on food we eat will likely be determined by decisions made based on specific pesticide usage and environmental and health assessments. In Asia, however, monitoring of insecticides on food and health concerns may take prominence over rulings on pesticide usage, particularly for exported crops.

Although the US EPA ban of most residential uses of organophosphates in 2001, as well as some for agricultural purposes, resulted in decreases in both the level and percentage of OP insecticides employed in the USA, approximately 20 million pounds of OP pesticides were still sprayed agriculturally on fruits and vegetables in 2012; representing 33% of all insecticides (EPA Pesticide Industry Sales and Usage 2008-2012 estimates). The most used OP, chlorpyrifos, which while now under pressure, still ranks as the fourteenth most commonly used conventional pesticide in the US and has recently been linked to autism and ADHD (EPA Revised Human Health Risk Assessment for Registration Review, November 2016). Aldicarb, the active substance in the pesticide Temik, is one of the most widely used insecticide and also one of the most environmentally toxic one. One consideration with banning all OPs is that, in contrast to other pesticides, they are hydrolyzed slowly in a moist atmosphere and in water and show a low propensity to move up the food chain as happened with DDT and other chlorohydrocarbons. However, in contrast to the USA, Australia and the European Union, which have banned or severely restricted many pesticides, their use in Asia and developing countries is still widespread and even parathion is still widely used despite its ban. Thus, a very large market will exist domestically and overseas for many years for OP/C pesticides alone. Moreover, monitoring use and residuals of other pesticides will become more and more important due to increasing awareness and concerns of environmental and health impact. Recent reports from Germany showed massive decline in insect population and diversity and this is becoming a major public concern for the use of insecticides in agriculture. A step increasing demand for rapid testing of environmental samples for pesticides including organophosphates is anticipated.

Several biosensor devices have been developed for detection of pesticides, OP insecticides and nerve agents based on electrical, amperometric, spectroscopic and color readouts. For example, available pesticide detection kits include NIDS Rapid Pesticide Test kit (ANP Technologies), Pesticide Detection cards (RenekaBio), and Agri-Screen Ticket kit (Neogen). However, these kits are multicomponent, have imprecise endpoints, require long incubation periods, and/or require chopping up food or testing fluids after washing. Thus, use of these kits at test sites to obtain rapid results (in less than 20 minutes), or to test more than 1,000 fruit/vegetables within a few hours (e.g. 1-8 hours), for example, is not practical or even possible, and cost-effective high-throughput screening of agricultural products for consumer safety and assurance is thus not feasible. However, rapid onsite testing is an essential prerequisite for withdrawing contaminated food from the market to efficiently protect consumers, and to detect illegal use.

Because the kits currently on the market to detect insecticides and other pesticides have been shown to have imprecise endpoints, require long incubation periods and use complex "kits" with several solutions, what is required is a more robust and self-contained test which detects OP/C rapidly (e.g., 2-20 minutes) and with high sensitivity and selectivity.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject.

As described herein, the innovative features are the engineering of the first efficient, small, inexpensive, hand-held device for rapid, sensitive and specific detection of organophosphate and carbamate compounds on surfaces, agricultural produce and environmental samples, without the need for sophisticated equipment.

As described herein, the invention relates to a device for detecting an OP/C compound comprising the following elements (1) a top piece comprising a first carrier material, wherein said first carrier material comprises an immobilized OP/C Detecting Enzyme; (2) a first substrate; (3) a second enzyme, (4) a second substrate; (5) a pH Sensitive Dye; (6) a second carrier material; (7) an ampoule comprising a buffer; (8) a middle piece and (9) a bottom piece, wherein the middle piece is associated with the top piece and the bottom piece, wherein the middle piece comprises the second carrier material and the ampoule, and wherein when the middle piece is turned relative to either the top piece or the bottom piece, the ampoule is capable of being cracked to release the buffer to contact the first carrier material and the second carrier material causing (i) the enzymatic conversion of the first substrate by the OP-detecting enzyme to produce an acidic reaction product; and (ii) the enzymatic conversion of the second substrate by the second enzyme to produce a basic reaction product. This device may also include an Oxidizer.

In preferred embodiments, the OP/C Detecting Enzyme is (a) a hydrolase; (b) a lipase, a phosphatase, an amylase, a cellulase, a protease, a peptidase, a urease or a deaminase; (c) a carboxylesterase (CES), acetylcholinesterase (AChE), butyrylcholinesterase (BChE), organophosphorus hydrolase or organophosphorus acid anhydrolase; (d) CES1 or CES2; (d) selected from Tables 2-5; or (e) an OP/C Detecting Enzyme Variant having at least 70%, at least 75%, at least 80%, at least 85%, at least 90, at least 91%, at least 92%, at least 93%, at least 94%, at least 95%, at least 96%, at least 97%, at least 98%, or at least 99% identity to the OP/C Detecting Enzyme amino acid sequence of (a)-(d). As described herein the OP/C Detecting Enzyme Variant both (1) retains the ability to hydrolyse the first substrate; and (2) maintains that ability to be inhibited by an OP/C.

In preferred embodiment, the OP/C Detecting Enzyme: (a) can detect at least 10 ug, at least 20 ug, at least 30 ug, at least 40 ug, at least 50 ug, at least 60 ug, at least 70 ug, at least 80 ug, at least 90 ug or at least 100 ug of an OP/C compound; (b) can detect between 10-100 ug, between 20-100 ug, between 30-100 ug, between 40-100 ug, between 50-100 ug, between 60-100 ug, between 70-100 ug, between 80-100 ug, between 90-100 ug of an OP/C compound; (c) comprises an inhibition rate constant $k_i$ of at least $10^3$ $M^{-1} \cdot min^{-1}$ to $10^8$ $M^{-1} \cdot min^{-1}$, at least $10^4$ $M^{-1} \cdot min^{-1}$ to $10^8 M^{-1} \cdot min^{-1}$, at least $10^5$ $M^{-1} \cdot min^{-1}$ to $10^8 M^{-1} \cdot min^{-1}$, at least $10^6$ $M^{-1} \cdot min^{-1}$ to $10^8 M^{-1} \cdot min^{-1}$, or at least $10^7$ $M^{-1} \cdot min^{-1}$ to $10^8 M^{-1} \cdot min^{-1}$; and/or (d) comprises an inhibition rate constant $k_i$ of $10^3$-$10^5$ $M^{-1} \cdot min^{-1}$, $k_i$ of $10^4$-$10^5$ $M^{-1} \cdot min^1$, $10^5$-$10^6$ $M^{-1} \cdot min^{-1}$, $10^6$ $M^{-1} \cdot min^{-1}$ to $10^7$ $M^{-1} \cdot min^{-1}$, or $10^6$ $M^{-1} \cdot min^{-1}$ to $10^8$ $M^{-1} \cdot min^{-1}$.

In preferred embodiments, the first carrier material is comprised of: (a) natural polymers, including but not limited to cellulose, hemicellulose, pectin, chitin, silk, lignin, starch, polypeptides, collagens, keratins, polysaccharides, nucleic acids, and/or rubbers; or (b) derivatives of natural polymers, including but not limited to methylation, carboxylation, amidation, sulfation, hydroxylation, condensation, iodination, reduction, oxidation, esterification, alkylation, and/or halogenation; and/or (c) synthetic polymers and copolymers, including but not limited to polyurethanes, thermoplastic polyurethanes, silicones, polyamides, polystyrenes, bakelite, polyethylene, polypropylene, polyvinyl chloride, Polytetrafluoroethylene, Polychloroprene, and/or polyimides. In preferred embodiments, the first carrier material is a sponge and/or is made of polyurethane.

In further embodiments, the first substrate is selected from acetylcholine, butyrylcholine4-nitrophenyl acetate, 4-nitrophenyl propionate, 4-nitrophenyl butyrate, 4-nitrophenyl valerate, 4-nitrophenyl dimethylacetate, 4-nitrophenyl trimethylacetate, 4-nitrophenyl 4-guanidinobenzoate, n-Glycero-3-phosphocholine, or 6-nitrocoumarin. First substrate may further be selected from Thioesters such as acetylthiocholine, butyrylthiocholine, S-4-Nitrobenzyl thioacetate, S-Phenyl-thioacetate.

In further embodiments, the second enzyme and second substrate is selected from Table 6. In further preferred embodiments, the second enzyme is urease, the second substrate is urea, and/or the basic reaction product is ammonia.

In further preferred embodiments, the pH Sensitive Dye is selected from nitrazine, phenol red, chlorophenol red, bromocresol green, cresoi red, bromomethyl blue, or bromocresol purple.

In certain embodiments, the Oxidizer is included in the device and converts an inactive OP/C compound to an active OP/C compound. Examples of such Oxidizers include, but are not limited to Fenton, a halogen (e.g. iodine, bromine, chlorine and fluorine), or a P450 enzyme in the presence of the cofactor NADPH. Preferred example of P450 enzyme is the wildtype or triple mutant of CYP1A2 (P450 BM-3 (CYP102-A1).

In preferred embodiments, besides the OP/C Detecting Enzyme, the first carrier material can further comprise the first enzyme, the second enzyme and/or the Oxidizer. In other embodiments, the ampoule further comprises the pH Sensitive Dye; and/or the second carrier material comprises the pH Sensitive Dye, the first substrate, the second substrate, and/or the Oxidizer.

In further preferred embodiments, the second carrier material is selected from: a test strip comprising dried filter paper or a second polymer.

In further preferred embodiments, the pH Sensitive Dye, the first substrate, the second substrate, and/or the Oxidizer are lyophilized as a microtablet.

In further preferred embodiments, the top piece and the middle piece are connected. Additionally, in preferred embodiments the ampoule extends into the bottom piece. In further embodiments, the middle piece contains one or more holes to permit flow of released contents of the ampoule between the bottom piece and the middle piece. Additionally, the device as described herein further comprises a lid, and this lid can be transparent and/or comprise a window.

In further preferred embodiments, the device comprises at least one O-ring that can be place in between the top piece and the middle piece and/or between the middle piece and the bottom piece to ensure sealing of the connected pieces so that the reaction solutions stay in place.

In additional preferred embodiments, the device is operably associated with a smart phone.

As described herein, additional embodiments include a method of detecting an OP/C comprising: (a) contacting the device as described herein with a surface; (b) turning the middle piece relative to either the top piece or the bottom piece thereby cracking the ampoule to release the buffer to contact the first carrier material and the second carrier material causing the enzymatic conversion of a second substrate by a second enzyme; and wherein: (1) in the absence of an OP/C, the enzymatic conversion of the first substrate by the OP/C Detecting Enzyme occurs, resulting in a maintenance of a baseline pH; or (2) in the presence of an OP/C, the enzymatic conversion of the first substrate by the OP/C Detecting Enzyme is inhibited by the OP/C compound, resulting in an increase in pH above the baseline pH due to the production of the basic reaction product.

As described herein and as known in the art, many OPs and carbamates can be detected using the device or the method. Particularly, the OP/C compound that can be detected includes but is not limited to: (a) an insecticide selected from: acephate, aldicarb (Temik), carbachol, carbamate, carbaryl (Sevin), carbofuran (Furadan), carisoprodol, chlorfenvinphos, Chlorophyrifos-oxon, Chlorphyrifos, Dementon-S, Diazoxon, diazinon, Dichlorvos, dicrotophos, dimethoate, dithiocarbamates, EA-3990, eserine, ethienocarb, ethoprophos, ethyl carbamate, felbamate, fenobucarb, fenamiphos, isocarbophos, Malathion, mebutamate, meprobamate, Methamidaphos, methomyl, methyl carbamate, methyl parathion, Methyl-POX, monocrotophos, naled, neostigmine, omethoate, oxamyl, Paraoxon, Parathion, phorate, phosmet, phosphamidon, rivastigmine, T-1123, terbufos, tetrachlorvinphos, Tetriso, thiocarbamates (e.g., O-thiocarbamate or S-thiocarbamates), triazophos, and/or tybamate; (b) a G agent, such as Tabun (GA), Sarin (GB), Chlorsarin (GC), Soman (GD), methylsarin, n-butylsarin, iso-butylsarin, n-propylsarin, ethylsarin (GE), and/or cyclosarin (GF), GV; (c) a V agent, such as EA-3148, VE, VG, VM, VP, VR, VS, and/or VX; and/or (d) a Novichok Agent, such as A-234.

As also described herein and in preferred embodiments, the device (a) can detect at least 10 ug, at least 20 ug, at least 30 ug, at least 40 ug, at least 50 ug, at least 60 ug, at least 70 ug, at least 80 ug, at least 90 ug or at least 100 ug of an OP/C compound; and/or (b) can detect between 10-100 ug, between 20-100 ug, between 30-100 ug, between 40-100 ug, between 50-100 ug, between 60-100 ug, between 70-100 ug, between 80-100 ug, between 90-100 ug of an OP/C compound.

Examples of surfaces that can be tested with the device as described herein include, but are not limited to food, clothing, or machinery.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

Embodiments are illustrated by way of example (and not limitation) in the figures of the accompanying drawings, in which like references, indicate similar elements and in which:

FIG. 1D shows the results of a second experiment demonstrating the in vitro conversion of parathion to paraoxon using cytochrome P450 (CYP1A2)/NADPH microsomes. Increased inhibition rate constants (ki) against rHuCES of parathion (L) and chlorpyrifos (R) following conversion to their oxons after a 10 min incubation with NADPH and P450(CYP) from two sources. Paraoxon was used as a control.

FIG. 2 shows a representative example of OP/C Detecting Enzyme sequences that can be used in the device as described herein.

DETAILED DESCRIPTION OF THE INVENTION

Figure 1A:
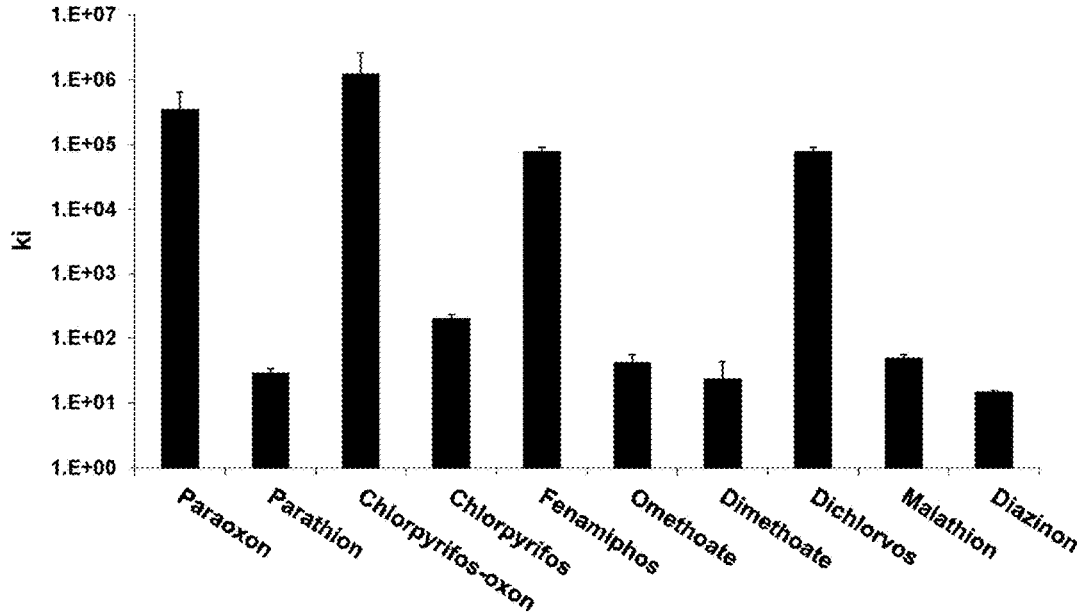
FIG. 1A shows the Bimolecular rate constants (ki) of plant-derived rHuCES (recombinant human carboxylesterase) extracts tested against a battery of OP insecticides.

Before describing the present invention in detail, it is to be understood that this invention is not limited to particularly exemplified materials or process parameters as such may, of course, vary. It is also to be understood that the terminology used herein is for the purpose of describing particular embodiments of the invention only and is not intended to be limiting of the use of alternative terminology to describe the present invention.

All publications, patents and patent applications cited herein, whether supra or infra, are hereby incorporated by reference in their entirety for all purposes.

A. Definitions

As used in this specification and the appended claims, the singular forms "a," "an" and "the" include plural nouns unless the content clearly dictates otherwise. For example, reference to "a polypeptide" includes a mixture of two or more such polypeptide molecules or a plurality of such polypeptide molecules. Similarly, reference to a "polynucleotide" includes a mixture of two or more such polynucleotide molecules or a plurality of such polynucleotide molecules.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

As used herein, "OP/C" is used to define an organophosphorus or carbamate insecticide or nerve agent. Representative examples of OP/Cs include, but are not limited to:

(a) an insecticide selected from: acephate, aldicarb (Temik, AgLogic 15G), carbachol, carbamate, carbaryl (Sevin), carbofuran (Furadan), carisoprodol, chlorfenvinphos, Chlorophyrifos-oxon, Chlorphyrifos, Dementon-S, Diazoxon, diazinon, Dichlorvos, dicrotophos, dimethoate, dithiocarbamates, EA-3990, eserine, ethienocarb, ethoprophos, ethyl carbamate, felbamate, fenobucarb, fenamiphos, isocarbophos, Malathion, mebutamate, meprobamate, Methamidaphos, methomyl, methyl carbamate, methyl parathion, Methyl-POX, monocrotophos, naled, neostigmine, omethoate, oxamyl, Paraoxon, Parathion, phorate, phosmet, phosphamidon, rivastigmine, T-1123, terbufos, tetrachlorvinphos, Tetriso, thiocarbamates (e.g., O-thiocarbamate or S-thiocarbamates), triazophos, and/or tybamate;

(b) a G agent, such as Tabun (GA), Sarin (GB), Chlorsarin (GC), Soman (GD), methylsarin, n-butylsarin, iso-butylsarin, n-propylsarin, ethylsarin (GE), and/or cyclosarin (GF), GV;

(c) a V agent, such as EA-3148, VE, VG, VM, VP, VR, VS, and/or VX; and/or (d) a Novichok Agent, such as A-234.

As all OP/Cs work by inhibiting the ability of an OP/C Detecting Enzyme to convert the first substrate, the OP/C can be detected using the same colorimetric assay described herein.

Although not formally classified as OPs, the mechanism of inhibiting AChE also occurs with carbamate insecticides/ nerve agents. Thus, the device described herein can also be used to detected carbamate agents, including carbamate and/or carbamate insecticides/nerve agents. Examples of such agents include, but are not limited to: aldicarb (Temik), carbofuran (Furadan), carbaryl (Sevin), ethienocarb, fenobucarb, oxamyl, methomyl, T-1123, EA-3990, ethyl carbamate, methyl carbamate, neostigmine, rivastigmine, meprobamate, carisoprodol, felbamate, mebutamate, tybamate, carbachol, thiocarbamates (e.g., O-thiocarbamate, S-thiocarbamates), and/or dithiocarbamates. As used herein, "OP" or "OPs" will include carbamate insecticides/nerve agents.

As used herein, an "OP/C Detecting Enzyme" refers to is (a) a hydrolase; (b) a lipase, a phosphatase, an amylase, a cellulase, a protease, a peptidase, a urease or a deaminase; (c) a carboxylesterase (CES), acetylcholinesterase (AChE), butyrylcholinesterase (BChE), organophosphorus hydrolase or organophosphorus acid anhydrolase; (d) CES1 or CES2; (d) selected from Tables 2-5; or (e) an OP/C Detecting Enzyme Variant having at least 70%, at least 75%, at least 80%, at least 85%, at least 90, at least 91%, at least 92%, at least 93%, at least 94%, at least 95%, at least 96%, at least 97%, at least 98%, or at least 99% identity to the OP/C Detecting Enzyme amino acid sequence of (a)-(d). As described herein the OP/C Detecting Enzyme Variant both (1) retains the ability to convert the first substrate into acetic acid; and (2) maintains that ability to be inhibited by an OP/C. As the sequences for these families of enzymes are known and published in public databases, they have not been included in the present specification, yet are hereby incorporated by reference in their entirety if necessary. Particularly, in preferred embodiments, the term "OP/C Detecting Enzymes" also includes variants of such CES, AChE, or BChE enzymes so long as the variant (a) has at least 70%, at least 75%, at least 80%, at least 85%, at least 90, at least 91%, at least 92%, at least 93%, at least 94%, at least 95%, at least 96%, at least 97%, at least 98%, or at least 99% identity to the amino acid sequence from which is was derived, (b) retains the ability to convert the first substrate into acetic acid and (c) maintains that ability to be inhibited by an OP/C. Those skilled in the art will readily acknowledge that the method according to this invention is not limited to any single enzymes or enzyme family and can generally be applied to enzymes that catalyze a first reaction that leads to a pH decrease. Thus, the device can be used for diverse reactions and enzymes including but not limited to hydrolases and oxidoreductases.

In preferred embodiments, the OP/C Detecting Enzyme: (a) can detect at least 10 ug, at least 20 ug, at least 30 ug, at least 40 ug, at least 50 ug, at least 60 ug, at least 70 ug, at least 80 ug, at least 90 ug or at least 100 ug of an OP/C compound; (b) can detect between 10-100 ug, between 20-100 ug, between 30-100 ug, between 40-100 ug, between 50-100 ug, between 60-100 ug, between 70-100 ug, between 80-100 ug, between 90-100 ug of an OP/C compound; (c) comprises an inhibition rate constant $k_i$ of at least $10^3$ $M^{-1} \cdot min^{-1}$ to $10^8$ $M^{-1} \cdot min^{-1}$, at least $10^4$ $M^{-1} \cdot min^{-1}$ to $10^8$ $M^{-1} \cdot min^{-1}$, at least $10^5$ $M^{-1} \cdot min^{-1}$ to $10^8$ $M^{-1} \cdot min^{-1}$, at least $10^6$ $M^{-1} \cdot min^{-1}$ to $10^8 M^{-1} \cdot min^{-1}$, or at least $10^7 M^{-1} \cdot min^{-1}$ to $10^8$ $M^{-1} \cdot min^{-1}$; and/or (d) comprises an inhibition rate constant $k_i$ of $10^3$-$10^5$ $M^{-1} \cdot min^{-1}$, $k_i$ of $10^4$-$10^5$ $M^{-1} \cdot min^{-1}$, $10^5$-$10^6$ $M^{-1} \cdot min^{-1}$, $10^6$ $M^{-1} \cdot min^{-1}$ to $10^7$ $M^{-1} \cdot min^{-1}$, or $10^6$ $M^{-1} \cdot min^{-1}$ to $10^8$ $M^{-1} \cdot min^{-1}$.

As used herein, when an OP/C is classified as "not detected" by the device as described herein, there still may be very low amounts of OP/C present on the surface. However, the amount is at a level that is below the limit of detection of the device.

As used herein "baseline pH" refers to the pH or pH change in the absence of any inhibitor of the first enzyme, i.e. the OP/C Detecting Enzyme. This baseline pH is set by the two reactions occurring within the device upon release of the buffer from the ampoule. Conversion of the first substrate by the first enzyme acidifies, i.e. decreases the pH the reaction buffer, and conversion of the second substrate by the second enzymes basifies, i.e. increases the reaction buffer. The reaction rates for the first and second reaction are chosen such that the overall change of the pH is zero (idealized) or decreases slightly, and the pH responsive molecule, e.g. the halochromic chemical compound (pH indicator), does not change its optical properties. However, in the presence of an inhibitor of the first enzyme, the reaction rate of the first reaction, and thus the acidification (decrease of the pH) due to conversion of the first substrate is reduced, thus resulting in a net increase in pH evidenced by the color change of the pH indicator. The speed and degree of the color change reflect the inhibition kinetics and the bimolecular rate constant (ki) of the first enzyme for the OP/C and amount of inhibitor present, i.e. OP/C pesticide for an OP/C Detecting Enzyme. In preferred embodiments, the increase in pH is indicated when at least 0.5, at least 1.0, at least 2.0, or at least 3.0 pH levels have been obtained. And in preferred embodiments, a product of the second reaction is ammonia.

As used herein, a "CES" is enzyme classified as a carboxylesterase, which is a well-studied, multigene family of enzymes (E.C. 3.1.1.1) broadly found in organisms ranging from bacteria to mammals. These enzymes are members of the serine hydrolase superfamily, in which a serine residue is involved in the hydrolysis of ester, amide, or carbamate bonds. See, e.g., Sogorb MA, Vilanova E. "Enzymes involved in the detoxification of organophosphorus, carbamate and pyrethroid insecticides through hydrolysis," Toxicol. Lett. (2002) 128:215-228. Organophosphate, carbamate, and pyrethroid insecticides are metabolized by CES. The OP/C binding site acyl-binding poket (Hopkins et al, Biochemistry (2017) 56:5512-5525). A recent genomic analysis defined five distinct mammalian CES subfamilies (Williams et al. 2010) based on the genetic sequence and genomic structure, with CES1 and CES2 subfamily proteins being most extensively studied. There are significant sequence similarities for the five CES families, especially for key regions previously identified for human liver CES1 (Bencharit et al. 2003, 2006; Fleming et al. 2005). Three-dimensional structural analyses of human CES1 have identified three major ligand binding sites, including the broad-specificity active site, the "side door," and the "Z-site," where substrates, fatty acids, and cholesterol analogs, respectively, are bound; and an active site 'gate', which may facilitate product release following catalysis (Bencharit et al. 2003, 2006; Fleming et al. 2005). The OP/C binding site acyl-binding pocket See, e.g., Holmes et al., Mamm. Genome. 2010 October; 21(9-10): 427-441 for further description of amino acid conservation between CES subfamilies, crystal structure, and conserved amino acids between different species of CES (herein incorporated by reference in its entirety). As used herein, any known CES enzymes (see, for example FIG. 2, Table 2, and/or the enzymes described in Holmes et al.) can be included in the device described herein and used to detect OP, as well as variants of such known CES enzymes that retain carboxylesterase activity. In preferred embodiments CES1 or CES2 enzymes (including variants) are used.

As used herein "AChE" refers to the class of proteins referred to as acetyl cholinesterase and "BChE" refers to the class of proteins referred to as butyrylcholinesterase ("BChE") (classified as EC 3.1.1.7 and EC 3.1.1.8 respectively). The 3D structure of acetylcholinesterase has been determined and published. [e.g., PMID: 1678899]. This protein has a 3-layer alpha-beta-alpha sandwich fold common to members of the alpha/beta hydrolase family. Surprisingly, given the high turnover number of acetylcholinesterase, the active site of these enzymes has been determined to be located at the bottom of a deep and narrow cleft, named the active-site gorge. As used herein, any known AChE/BChE enzyme can be included in the device described herein and used to detect OP, as well as variants of such known AChE/BChE enzymes. Representative examples of such AChE/BChE enzymes are shown in Tables 2-5 and FIG. 2.

As used herein, a "first substrate" is used to refer to a molecule that can be enzymatically converted into an acid by the first enzyme, e.g. an OP/C Detecting Enzyme. Representative examples of a first substrate include, but are not limited to acetylcholine, acetylthiocholine, butyrylcholine, butyrylthiocholine, 4-nitrophenyl acetate, 4-nitrophenyl propionate, 4-nitrophenyl butyrate, 4-nitrophenyl valerate, 4-nitrophenyl dimethylacetate, 4-nitrophenyl trimethylacetate, 4-nitrophenyl 4-guanidinobenzoate, or 6-nitrocoumarin. See, for example, Williams et al., Drug Metabolism and Disposition, Vol. 39, No. 12 (2011) (incorporated by reference in its entirety).

As used herein a "pH Sensitive Dye" refers to an indicator composition that is capable of undergoing an observable change of state (for example, a change in optical properties/color) as a result of the reactions taking place within the device. Preferably, such a dye changes optical properties in a manner that is visible to the human eye. Examples of pH-sensitive dyes include, but are not limited to: nitrazine, phenol red, chlorophenol red, bromocresol green, cresol red, bromomethyl blue, or bromocresol purple. The degree of color change can be correlated to the amount of conversion of the first substrate. Therefore, color change of varying degree not only indicates the presence of an OP/C, but also the inhibition kinetics and the quantity of OP/C present.

As described herein, the conversion of the second substrate by the second enzyme results in basification of the reaction buffer (i.e., the act or process of making something more basic resulting in the raising of the pH of something). Representative examples of a second substrate and second enzyme include, but are not limited to urea and urease (classified as EC 3.5.1.5), urea and urea amidolyase (classified as EC 6.3.4.6 and EC 3.5.1.54), biuret and biuret amidohydrolase (classified as EC 3.5.1.84), [beta-hydroxy-pyruvate+glycolaldehyde] and transketolase (classified as EC 2.2.1.1, with representative examples of substrates being: D-fructose 6-phosphate, D-glyceraldehyde 3-phosphate, D-ribose 5-phosphate, or D-xylulose 5-phosphate), adenosine and adenosine deaminase (classified as EC3.5.4.4), adenine and adenine deaminase (classified as EC 3.5.4.15), guanosine and guanosine deaminase (classified as EC 3.5.4.15), guanine and guanine deaminase (classified as EC 3.5.4.3), cytosine and cytosine deaminase (classified as EC 3.5.4.5).

Figure 8:
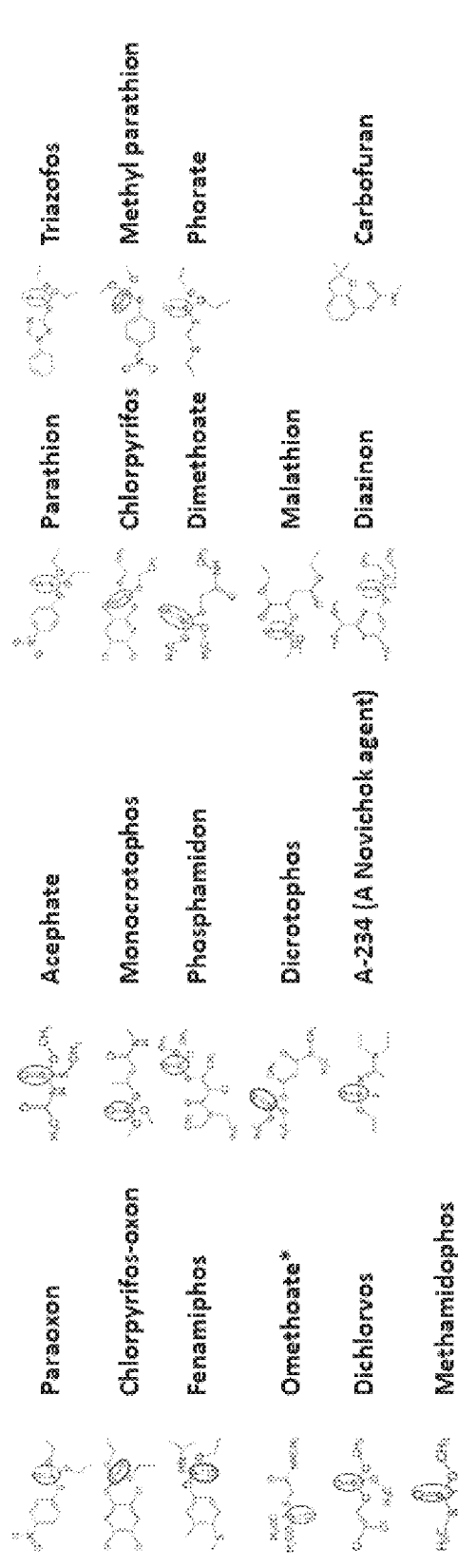
FIG. 8 shows the structures of the most commonly used OP insecticides showing the presence of P=O and P=S bonds which determine their bimolecular rate constants and toxicity against rHuCES. It should be noted that currently omethoate is the only exception in that it has a P=O bond and a low ki ($10^1$ $M^{-1} \cdot min^{-1}$) against CES possibly related to the leaving group slowing the reaction or a steric hindrance effect. A carbamate is included since they also inhibit AChE and CES.

As used herein, an "Oxidizer" is used to refer to a molecule capable of converting an inactive phosphorothionate "thion" or carbamate form of an OP/C into an active (e.g. oxon) form (see FIG. 8). Representative examples of an Oxidizer but are not limited: to Fenton, a halogen (e.g. iodine, bromine, chlorine and fluorine), or a P450 enzyme in the presence of the cofactor NADPH. Preferred example of P450 enzyme is a triple mutant of CYP1A2 (P450 BM-3 (CYP102-A1).

In the present invention, a "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The terms "percent (%) sequence similarity", "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wisconsin), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/on the WorldWideWeb.

Another non-limiting example of a mathematical algorithm utilized for the comparison of sequences is the algorithm of Myers and Miller, CABIOS 1988; 4: 1 1-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, MA; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In the present invention, "isolated polypeptide" means the polypeptide is separated from its environment and present in sufficient quantity to permit its identification or use. Isolated polypeptides include recombinantly produced polypeptides. This means, for example, the polypeptide may be (i) selectively produced by expression cloning or (ii) purified by chromatography or electrophoresis. Isolated proteins or polypeptides may be, but need not be, substantially pure. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, e.g., isolated from other proteins. Any of the peptides or polypeptides provided herein may be isolated.

B. Device

As described herein the "device" is designed to contain all sensing components in a self-enclosed system which is substantially simpler to manufacture and use as compared to the ten or more components used for other pens currently on the market to detect nerve agents. This innovation provides for an efficient, small, inexpensive, hand-held device for rapid, sensitive and specific detection of OP/C.

Figure 3:
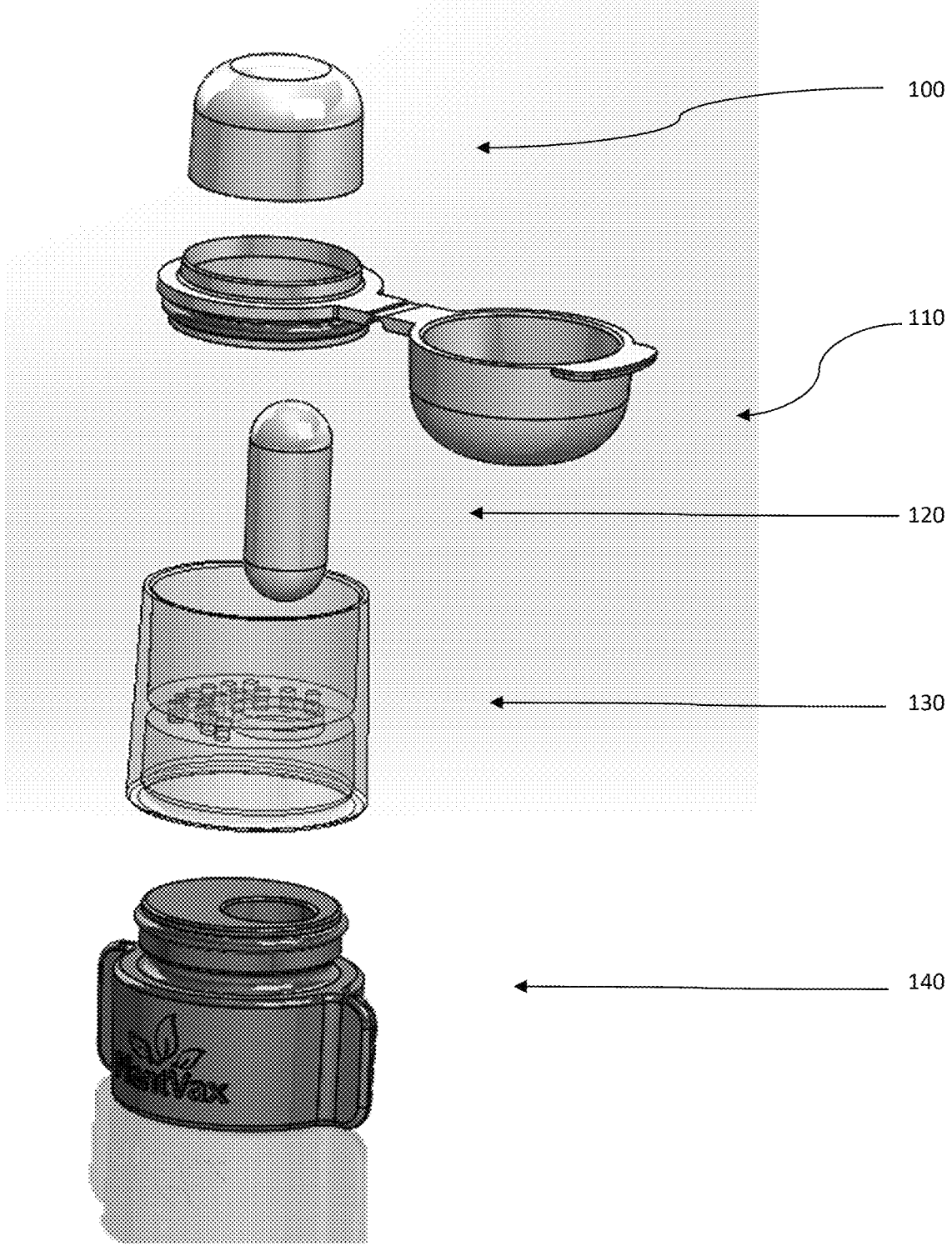
FIG. 3 shows the individual different components of the device.
Figure 4:
FIG. 4 shows a top view of the device.
Figure 5:
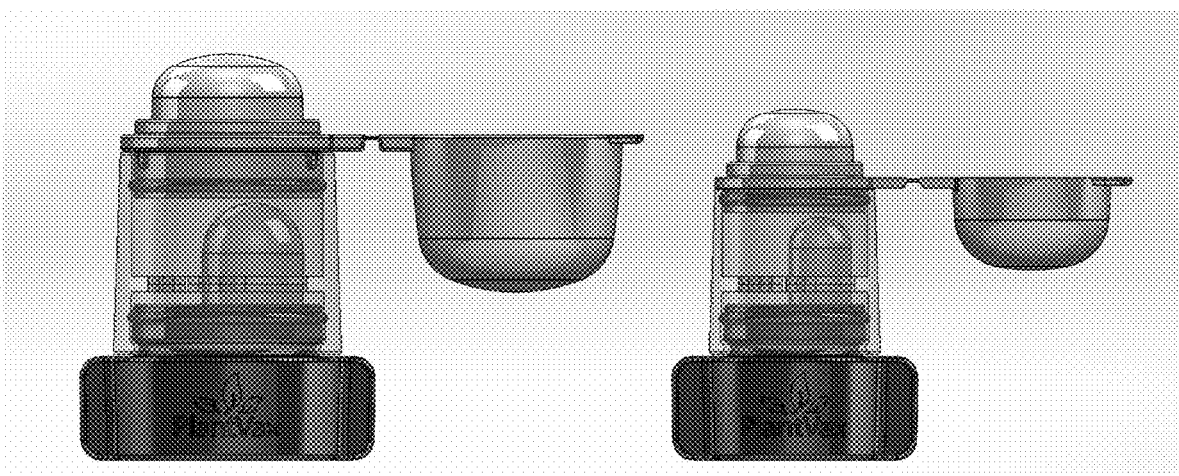
FIG. 5 shows the side view of the device.
Figure 6:
FIG. 6 shows a close-up view of the device.
Figure 7:
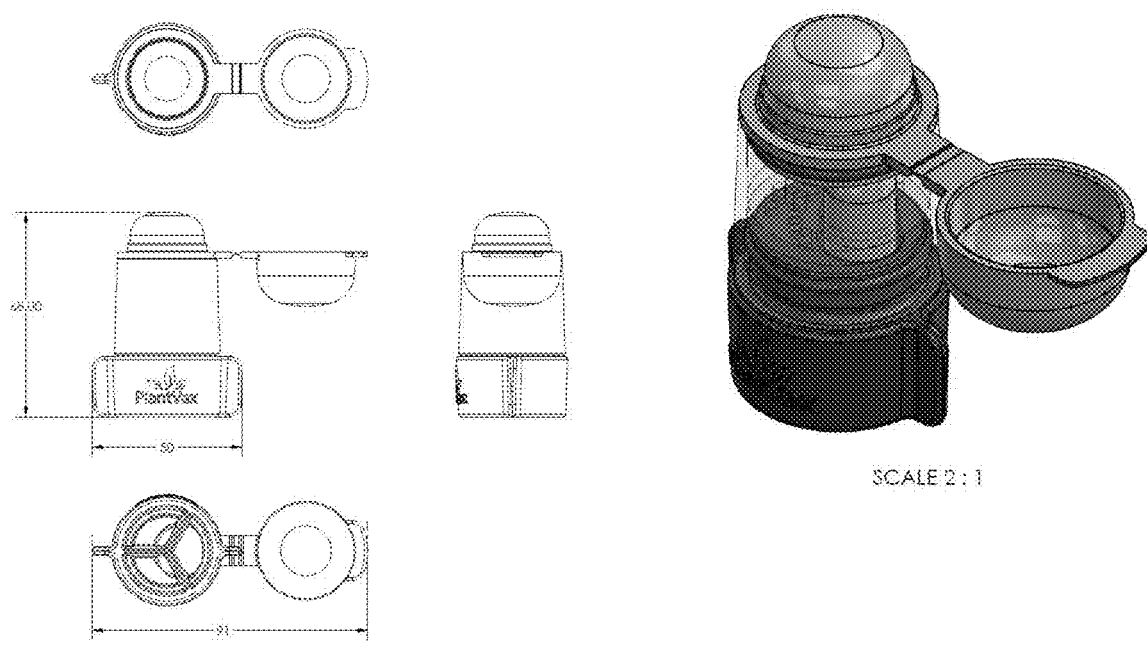
FIG. 7 shows a further schematic of the device.

As shown in FIG. 3, the device described herein comprise the following components: a first carrier material (100) which fits into a top piece (110). An ampoule (120) is contained within and protected by a middle piece (130) which attaches to a bottom piece (140). The ampoule can be optionally be also within the bottom piece. The device can optionally also comprise a separate cap or lid, alternatively, as shown in FIG. 3, the top piece (110) can be manufactured to include a cap or lid. Besides the ampoule (120), the middle piece (130) also houses a second carrier material (not shown).

The substrates and enzymes that are used to detect the OP/C can be configured differently within the device. For example, the substrates, enzymes and pH sensitive dye can be configured in the following different embodiments based on intended use. For example, short term storage can allow for the enzymes, substrates and/or dyes to be included in the ampoule. In contrast, long term storage would have a preferred configuration where only the buffer would be included in the ampoule. In further preferred embodiments, the matching substrates and enzymes should not be configurated in the same location within the device.

13

TABLE 1

| First carrier material | Ampoule | Second carrier materials |
|---|---|---|
| 1st Enzyme [1] | Buffer | 2nd Enzyme<br>1st and 2nd substrate<br>pH Dependent Dye |
| 1st Enzyme<br>pH Dependent Dye | Buffer | 2nd Enzyme<br>1st and 2nd substrate |
| 1st Enzyme | Buffer<br>pH Dependent Dye | 2nd Enzyme<br>1st and 2nd substrate |
| 1st and 2nd Enzyme | Buffer | 1st and 2nd substrate<br>pH Dependent Dye |
| 1st and 2nd Enzyme<br>pH Dependent Dye | Buffer | 1st and 2nd substrate |
| 1st and 2nd Enzyme<br>pH Dependent Dye | Buffer<br>2nd substrate | 1st substrate |
| 1st and 2nd Enzyme<br>pH Dependent Dye | Buffer<br>1st substrate | 2nd substrate |
| 1st and 2nd Enzyme<br>pH Dependent Dye | Buffer<br>1st and 2nd substrate | Empty |
| 1st Enzyme<br>pH Dependent Dye | Buffer | 1st and 2nd substrate |
| 1st and 2nd Enzyme<br>pH Dependent Dye | Buffer | 1st and 2nd substrate |
| 1st Enzyme | Buffer<br>2nd substrate | 1st substrate<br>2nd Enzyme<br>pH Dependent Dye |
| 1st Enzyme<br>pH Dependent Dye | Buffer<br>2nd substrate | 1st substrate<br>2nd Enzyme |
| 1st Enzyme | Buffer<br>2nd substrate<br>pH Dependent Dye | 1st substrate<br>2nd Enzyme |
| 1st and 2nd Enzyme | Buffer<br>2nd substrate | 1st substrate<br>pH Dependent Dye |
| 2nd Enzyme | Buffer | 1st Enzyme<br>1st and 2nd substrate<br>pH Dependent Dye |
| 2nd Enzyme<br>pH Dependent Dye | Buffer | 1st Enzyme<br>1st and 2nd substrate |
| 2nd Enzyme | Buffer<br>pH Dependent Dye | 1st Enzyme<br>1st and 2nd substrate |
| 2nd Enzyme | Buffer<br>2nd substrate | 1st Enzyme<br>1st substrate<br>pH Dependent Dye |
| 2nd Enzyme<br>pH Dependent Dye | Buffer<br>2nd substrate | 1st Enzyme<br>1st substrate |
| pH Dependent Dye | Buffer | 1st and 2nd Enzyme |
| 1st Enzyme | Buffer<br>1st and 2nd substrate | pH Dependent Dye<br>2nd Enzyme |

[1] e.g. OP/C detecting Enzyme

Within the context of this invention the term "buffer" means a composition (any combination) of water+/−solutes (including salts including but not limited to NaCl, KCl, MgSO4, CaCl, NiCl2, CuCl2) a pH buffering compound (including salts including but not limited to Tris, MES, HEPES, Phosphate, Citrate), a reducing agent or anti-oxidant (2-ME, DTT, Na2S2O5, ascorbic acid, glutathione, Cystine), an excipient (glucose, sucrose, glycerol, mannitol, proline, arginine, trehalose, erythritol, imidazol), a detergent (Tween-20, Tween-80, Triton-X100, Triton-X114, deoxycholic acid, maltoside, octyl-thioglucoside, CHAPS), a stabilizer (polyvinylpyrrolidone, chitosan, gelatin, elastin-like peptides, PEG, dendrimers, serum albumin, radical scavengers, Butylated hydroxytoluene, alkylated diphenylamine), preservative (benzoic acid, sulfur dioxide, gallic acid) or chelators of metal ions (ETDA, EGTA).

For example, the substrates and colorimetric reporters are dried onto the second carrier housed in the middle piece (130), along with a glass ampoule (120) filled with dilute buffer. The enzymes (either the OP/C Detecting Enzyme and/or the second enzyme) can be immobilized covalently or non-covalently on the first carrier material (100). The carrier materials (either the first and/or the second carrier material) can be a natural polymer, including but not limited to cellulose, hemicellulose, pectin, chitin, silk, lignin, starch, polypeptides, collagens, keratins, polysaccharides, nucleic acids, and/or rubbers; or (b) derivatives of natural polymers, including but not limited to methylation, carboxylation, amidation, sulfation, hydroxylation, condensation, iodination, reduction, oxidation, esterification, alkylation, and/or halogenation; and/or (c) synthetic polymers and copolymers, including but not limited to polyurethanes, thermoplastic polyurethanes, silicones, polyamides, polystyrenes, bakelite, polyethylene, polypropylene, polyvinyl chloride, Polytetrafluoroethylene, Polychloroprene, and/or polyimides) separated by the top piece (110) at the top of the device. In one embodiment, the OP/C Detecting Enzyme and, optionally, the pH Dependent Dye are incorporated into the polymer matrix of the first carrier material during synthesis of the polymer. For example, if polyurethane is used, the first carrier material can be formed by mixing water, the OP/C Detecting Enzyme, optionally the pH Dependent Dye, and an isocyanate functionalized polyurethane prepolymer, which incorporates the OP/C Detecting Enzyme, optionally the pH Dependent Dye into the polymer network. See, for example, U.S. Pat. No. 6,291,200 (incorporated by reference in its entirety).

In a further embodiment, the second carrier material can comprise lyophilized substrate(s) and enzyme(s), for example, in the form of a powder, film or tablet. In another embodiment, the substrate(s), pH dependent dye and/or the enzyme(s) can be spatially separated on the second carrier material, for example, by drying the components on separate pieces. In yet another embodiment, the second carrier material can be comprised of two or more materials, for example, two different filter papers, or a filter paper and a tablet, or two different tablets.

To employ, the user simply activates the chemistry by, in preferred embodiments, cracking the ampoule (120) and dissolving and mixing the components, then shaking the device or optionally pressing a valve which wets the first carrier material (100). The user then simply removes the cap and wipes the top piece of the device on the contaminated surface. Alternatively, the first carrier material (100) (with open cap) can be wiped on the wet or wetted surface, the cap be closed, the ampoule be cracked, the released components be mixed and distributed by shaking, followed by observation of the color change.

The user can then replace the cap and monitor the color of the first carrier material (100) for up to 5, 10, 15, etc. minutes to detect any color change. Ideally, the entire system is self-contained, with no waste or leaks, and presents virtually no hazard to the user. Further, because the first carrier material (100) is made up of an adsorptive material it can effectively pick up OPs from the surface with very high efficiency. The device leverages the high selectivity of the enzyme system for the OP/C inhibitor while ignoring nearly all environmental interferents, and also provides a nearly thousand-fold amplification of signal thanks to the unique dynamic buffering equilibrium response mechanism.

In preferred embodiments, the device is 68 mm high×50 mm wide. In the final optimized pen, some of the enzymes, substrates, ampoule and dye may be in different compartments but the chemistry may be the same.

To deploy and activate the chemistry the user simply breaks the ampoule (120) by holding the middle piece (130) with one hand and twisting the bottom piece (140) 90 degrees with the other hand; dissolving the chemicals contained in the second carrier material, e.g., dried paper (urea, a pH sensitive colorimetric yellow to red dye, and enzyme substrates e.g. 4-nitrophenol acetate (4-NPA). After cracking the ampoule (120), the device is inverted, and gravity and some gentle shaking mixes the buffer with the second carrier material containing the substrates and then the first carrier material (100) with embedded OP/C Detecting Enzyme while the cap is still on. The user then opens the cap, swabs the contaminated surface with the inverted pen; pressing down on the first carrier material (100) several times to wet the first carrier material (100) and ensure proper sampling. The cap is replaced, and the color of the first carrier material is monitored for 5-10 minutes to detect any change. The entire system is self-contained, with no waste or leaks, and presents virtually no hazard to the user. Further, the first carrier material is made of adsorptive material for the chemicals and picks them up from the surface with very high efficiency. The device leverages the high selectivity of the enzyme system for the OP/C inhibitor while ignoring nearly all environmental interferents, and also provides a nearly thousand-fold amplification of signal thanks to the unique dynamic buffering equilibrium response mechanism

C. Reaction Used to Detect OP/C

In the absence of OP/Cs, the device relies on an enzymatic reaction catalyzed by an OP/C Detecting Enzyme on a first substrate resulting in acidic reaction products to decrease the pH. At the same time, the second reaction system comprising the second enzyme and a second substrate produces basic reaction products which increase pH. The reaction rates of the first and second reaction are adjusted such that the net change of the pH is zero or decreases slightly. This sets the baseline pH. However, if OPs are present on a surface and transferred to the first carrier material of the device, the OP/C Detecting Enzyme is inhibited and unable to convert the first substrate and thereby decrease the pH. Thus, inhibition of the OP/C Detecting Enzyme by a pesticide or OP/C results in a net increase of the pH of the system over the baseline pH. By a pH Dependent Dye in the device, a change in pH can be reported by a change in color.

For example, U.S. Pat. No. 6,861,252 (hereby incorporated by reference in its entirety) teaches that a pH responsive colorimetric dye rapidly changes from yellow to red when OP/C nerve agents are detected (see, for example, FIG. 2 of this patent). When the OP/C Detecting Enzyme (this patent exemplifies AChE) is inhibited by an OP, substrate hydrolysis and the concurrent decrease in pH shuts off, and the base-producing second enzyme continues to make ammonia driving the system pH dramatically from e.g. 5 to 8. A colorimetric pH-responsive dye (pKa 6.5) is in turn titrated from yellow to red, providing a localized visual assessment of the presence of the OP/C. As described herein, this colorimetric reaction can be used in combination with the device to detect OP/C.

As a further example, nitrazine yellow dye can be used in the device described herein to detect OPs. For example, a nitrazine yellow dye can be incorporated into the first carrier material making up the first carrier material. In preferred embodiments, the synthesized first carrier material has a dye content of approximately 0.4 mg dye/g dry polymer. Physical property differences clearly visible to the naked human eye occur when the polymers were incubated within aqueous solutions of varying pH. The color of the samples ranges from bright orange at pH 6.5 to blue at pH 9.0. Distinctions in color were clearly discernable to the naked eye between each of samples exposed to a pH of 6, 6.4, 68, 7.2, 7.6, 8, 8.5 and 9. The series of colors observed in the polymers of the present invention was the same as the series of colors that is produced by suspending the soluble dye within aqueous solution (e.g., in the Ampoule (120)) over the same pH range.

Moreover, one approach proposed in this application is the use of CES rather than AChE or BChE as the OP/C Detecting Enzyme. We have found that the inhibition constants for OP/C insecticides are much higher (100-1000 fold) for CES than for AChE. Thus, CES enzymes are preferably used in the device to detect OP/C insecticides.

Additionally, variants can be created using standard mutational tools to generate improved variants that have improved sensitivity to different forms of OP/C insecticides so as to be inhibited at lower concentrations of the OP/C pesticides as compared to the protein from which the variant is derived. For example, enzymes and proposed mutants that can be used to detect OP/C pesticides are selected from:

a. Wild type carboxylesterase αE7 from the Australian blow fly *Lucilia cuprina* (LcαE7);

b. mutant form of LcαE7$^{G137D}$ c. LcαE7 mutants E183, K275, E78 and/or E292 d. Wild type AChE;

e. Mutant AChE, such as as rHuAChE containing two mutations in the acyl pocket residues (F295L, F297V);

f. Carboxylesterase (Cqestβ2) from the *Culex quinque-fasciatus* mosquito g. Any one of the enzymes listed in Tables 2-5.

Specially, one approach is to produce the blow fly wild type CES LcαE7 and mutated forms of LcαE7 (e.g, LcαE7$^{G137D}$). See, GenBank Accession Q25252_LUCCU for wildtype sequence. It should be noted that recombinant LcαE7 produced in the *E. coli* system is monomeric and dimeric while native human CES is trimeric. To examine how trimerization occurs, crystal structures of trimeric human CES produced in HEK293-derived hCES1 have been studied by de Sousa et al. which revealed that trimers were generated by the space group symmetry with the K78:E183 and K275:E292 salt bridges. Since the LcαE7 sequence contains the E183 and K275 but not the E78 or E292, a mutant of LcαE7 expressing all four of these amino acids have been produced in order to generate trimers with potentially increased stability.

TABLE 2

| | | Enzymes Classified as EC 3.1.1.8 | |
| --- | --- | --- | --- |
| Entry | Entry name | Protein names | Organism |
| Q95000 | CHLE1_BRALA | Cholinesterase 1 (Fragment) | *Branchiostoma lanceolatum* (Common lancelet) (*Amphioxus lanceolatum*) |
| Q95001 | CHLE2_BRALA | Cholinesterase 2 (Fragment) | *Branchiostoma lanceolatum* (Common lancelet) (*Amphioxus lanceolatum*) |

TABLE 2-continued

| | Enzymes Classified as EC 3.1.1.8 | | |
|---|---|---|---|
| Entry | Entry name | Protein names | Organism |
| P06276 | CHLE_HUMAN | Cholinesterase (Acylcholine acylhydrolase) (Butyrylcholine esterase) (Choline esterase II) (Pseudocholinesterase) | *Homo sapiens* (Human) |
| P32751 | CHLE_MACMU | Cholinesterase (Acylcholine acylhydrolase) (Butyrylcholine esterase) (Choline esterase II) (Pseudocholinesterase) (Fragment) | *Macaca mulatta* (Rhesus macaque) |
| Q5UR02 | CHLE_MIMIV | Probable cholinesterase (Acylcholine acylhydrolase) | *Acanthamoeba polyphagamimivirus* (APMV) |
| P32749 | CHLE_BOVIN | Cholinesterase (Acylcholine acylhydrolase) (Butyrylcholine esterase) (Choline esterase II) (Pseudocholinesterase) | *Bos taurus* (Bovine) |
| P32750 | CHLE_CANLF | Cholinesterase (Acylcholine acylhydrolase) (Butyrylcholine esterase) (Choline esterase II) (Pseudocholinesterase) (Fragment) | *Canis lupus familiaris* (Dog) (*Canis familiaris*) |
| O62760 | CHLE_FELCA | Cholinesterase (Acylcholine acylhydrolase) (Butyrylcholine esterase) (Choline esterase II) (Pseudocholinesterase) | *Felis catus* (Cat) (*Felis silvestris catus*) |
| P81908 | CHLE_HORSE | Cholinesterase (Acylcholine acylhydrolase) (Butyrylcholine esterase) (Choline esterase II) (EQ-BCHE) (Pseudocholinesterase) | *Equus caballus* (Horse) |
| Q03311 | CHLE_MOUSE | Cholinesterase (Acylcholine acylhydrolase) (Butyrylcholine esterase) (Choline esterase II) (Pseudocholinesterase) | *Mus musculus* (Mouse) |
| O62761 | CHLE_PANTT | Cholinesterase (Acylcholine acylhydrolase) (Butyrylcholine esterase) (Choline esterase II) (Pseudocholinesterase) | *Panthera tigris tigris* (Bengal tiger) |
| P32752 | CHLE_PIT | Cholinesterase (Acylcholine acylhydrolase) (Butyrylcholine esterase) (Choline esterase II) (Pseudocholinesterase) (Fragment) | *Sus scrofa* (Pig) |
| P21927 | CHLE_RABIT | Cholinesterase (Acylcholine acylhydrolase) (Butyrylcholine esterase) (Choline esterase II) (Pseudocholinesterase) | *Oryctolagus cuniculus* (Rabbit) |
| P32753 | CHLE_SHEEP | Cholinesterase (Acylcholine acylhydrolase) (Butyrylcholine esterase) (Choline esterase II) (Pseudocholinesterase) (Fragment) | *Ovis aries* (Sheep) |

TABLE 3

| | Enzymes Classified as EC 3.1.1.1 | | | |
|---|---|---|---|---|
| Entry | Entry name | Protein names | Gene Name | Organism |
| A1CFK9 | PATB_ASPCL | Carboxylesterase patB (Patulin synthesis protein B) | patB ACLA_093570 | *Aspergillus clavatus* (strain ATCC 1007/CBS 513.65/ DSM 816/NCTC 3887/NRRL 1) |
| A0A075TXZ3 | PATB_PENEN | Carboxylesterase patB (Patulin synthesis cluster protein B) | patB PEX2_082800 | *Penicillium expansum* (Blue mold rot fungus) |
| D4AV38 | LIP4_ARTBC | Probable secreted lipase ARB_00047 | ARB_00047 | *Arthroderma benhamiae* (strain ATC CMYA-4681/CBS 112371) (*Trichophyton mentagrophytes*) |
| Q4F883 | SG101-ARATH | Senescence-associated carboxylesterase 101 | SAG101 At5g14930 F2G14.50 | *Arabidopsis thaliana* (Mouse-ear cress) |
| O31452 | YBFK_BACSU | Carboxylesterase YbfK | ybfK BSU02260 | *Bacillus subtilis* (strain 168) |
| Q8VCT4 | CESD1_MOUSE | Carboxylesterase 1D (Carboxylesterase 3) (EC 3.1.1.67) (Fatty acid ethyl ester synthase) (FAEE synthase) (Triacylglycerol hydrolase) (TGH) | Ces1d Ces1 Ces3 | *Mus musculus* (Mouse) |
| P16303 | CES1D_RAT | Carboxylesterase 1D (Carboxyesterase ES-10) (Carboxylesterase 3) (EC 3.1.1.67) (ES-HVEL) (Fatty acid ethyl ester synthase) (FAEE synthase) (Liver carboxylesterase 10) (pI 6.1 esterase) | Ces1d Ces3 | *Rattus norvegicus* (Rat) |
| Q91WU0 | CES1F_MOUSE | Carboxylesterase 1F (Carboxylic ester hydrolase) (Triacylglycerol hydrolase 2) (TGH-2) | Ces1f CesML1 | *Mus musculus* (Mouse) |
| Q9SMM9 | CXE13_ARATH | Probable carboxylesterase 13 (AtCXE13) | CXE13 At3g48700 T8P19.210 | *Arabidopsis thaliana* (Mouse-ear cress) |
| Q9LVB8 | CXE20_ARATH | Probable carboxylesterase 120 (AtCXE20) | CXE20 At5g62180 MMI9.26 | *Arabidopsis thaliana* (Mouse-ear cress) |
| Q9SX78 | CXE2_ARATH | Probable carboxylesterase 2 (AtCXE2) | CXE2 At1g47480 F16N3.25 | *Arabidopsis thaliana* (Mouse-ear cress) |
| Q9FX92 | CXE3_ARATH | Probable carboxylesterase 3 (AtCXE3) | CXE3 At1g49640 F14J22.12 | *Arabidopsis thaliana* (Mouse-ear cress) |
| Q9FG13 | CXE15_ARATH | Probable carboxylesterase 15 (AtCXE15) | CXE15 At5g06570 F15M7.10 | *Arabidopsis thaliana* (Mouse-ear cress) |

TABLE 3-continued

Enzymes Classified as EC 3.1.1.1

| Entry | Entry name | Protein names | Gene Name | Organism |
|---|---|---|---|---|
| Q9FX93 | CXE4_ARATH | Probable carboxylesterase 4, mitochondrial (AtCXE4) | CXE4 At1g49650 F14J22.21 | *Arabidopsis thaliana* (Mouse-ear cress) |
| Q9LK21 | CXE11_ARATH | Probable carboxylesterase 11 (AtCXE11) | CXE11 At3g27320 K17E12.14 | *Arabidopsis thaliana* (Mouse-ear cress) |
| Q9SMN0 | CXE12_ARATH | Probable carboxylesterase 12 (AtCXE12) | CXE12 At3g48690 T8P19.200 | *Arabidopsis thaliana* (Mouse-ear cress) |
| Q8LED9 | CXE16_ARATH | Probable carboxylesterase 16 (AtCXE16) | CXE16 At5g14310 F18022.100 | *Arabidopsis thaliana* (Mouse-ear cress) |
| Q9LFR7 | CXE17_ARATH | Probable carboxylesterase 17 (AtCXE17) | CXE17 At5g16080 F1N13.220 | *Arabidopsis thaliana* (Mouse-ear cress) |
| Q9LT10 | CXE18_ARATH | Probable carboxylesterase 18 (AtCXE18) | CXE18 At5g23530 MQM1.21 | *Arabidopsis thaliana* (Mouse-ear cress) |
| O64641 | CXE9_ARATH | Probable carboxylesterase 9 (AtCXE9) | CXE9 At2g45610 F17K2.14 | *Arabidopsis thaliana* (Mouse-ear cress) |
| Q0ZPV7 | CXE1_ACTER | Carboxylesterase 1 (AeCXE1) | CXE1 | *Actinidia eriantha* (Velvet vine) (*Actinidia fulvicoma* var. *lanata*) |
| Q9LMA7 | CXE1_ARATH | Probable carboxylesterase 1 (AtCXE1) | CXE1 At1g19190 T29M8.6 | *Arabidopsis thaliana* (Mouse-ear cress) |
| Q9FX94 | CXE5_ARATH | Probable carboxylesterase 5 (AtCXE5) | CXE5 At1g49660 F14J22.11 | *Arabidopsis thaliana* (Mouse-ear cress) |
| Q9SX25 | CXE6_ARATH | Probable carboxylesterase 6 (AtCXE6) | CXE6 At1g68620 F24J5.14 | *Arabidopsis thaliana* (Mouse-ear cress) |
| Q9ZQ91 | CXE7_ARATH | Probable carboxylesterase 7 (AtCXE7) | CXE7 At2g03550 T4M8.1 | *Arabidopsis thaliana* (Mouse-ear cress) |
| O64640 | CXE8_ARATH | Probable carboxylesterase 8 (AtCXE8) | CXE8 At2g45600 17K2.13 | *Arabidopsis thaliana* (Mouse-ear cress) |
| B3PI89 | BIOHC_CELJU | Biotin biosynthesis bifunctional protein BioHC [Includes: Carboxylesterase BioH (Biotin synthesis protein BioH); Malonyl-[acyl-carrier protein] O-methyltransferase (Malonyl-ACP O-methyltransferase) (EC 2.1.1.197) (Biotin synthesis protein BioC)] | bioC CJA_0428 | *Cellvibrio japonicus* (strain Ueda107) (*Pseudomonas fluorescens* subsp. *cellulosa*) |
| Q21FY5 | BIOHC_SACD2 | Biotin biosynthesis bifunctional protein BioHC [Includes: Carboxylesterase BioH (Biotin synthesis protein BioH); Malonyl-[acyl-carrier protein] O-methyltransferase (Malonyl-ACP O-methyltransferase) (EC 2.1.1.197) (Biotin synthesis protein BioC)] | bioC Sde_3137 | *Saccharophagus degradans* (strain 2-40/ATCC 43961/DSM 17024) |
| C5BMZ8 | BIOHC_TERTT | Biotin biosynthesis bifunctional protein BioHC [Includes: Carboxylesterase BioH (Biotin synthesis protein BioH); Malonyl-[acyl-carrier protein] O-methyltransferase (Malonyl-ACP O-methyltransferase) (EC 2.1.1.197) (Biotin synthesis protein BioC)] | bioC TERTU_0492 | *Teredinibacter turnerae* (strain ATCC 39867/T7901) |
| Q5NUF3 | HIDH_SOYBN | 2-hydroxyisoflavanone dehydratase (EC 4.2.1.105) (Carboxylesterase HIDH) | HIDH Glyma01g45020 | *Glycine max* (Soybean) (*Glycine hispida*) |
| Q5NUF4 | HIDM_GLYEC | 2-hydroxyisoflavanone dehydratase (EC 4.2.1.105) (Carboxylesterase HIDM) | HIDM | *Glycyrrhiza echinata* (Licorice) |
| P81098 | SFAH_HELAN | Seed fatty acyl-ester hydrolase (Fragment) | | *Helianthus annuus* (Common sunflower) |
| P23141 | EST1_HUMAN | Liver carboxylesterase 1 (Acyl-coenzyme A:cholesterol acyltransferase) (ACAT) (Brain carboxylesterase hBr1) (Carboxylesterase 1) (CE-1) (hCE-1) (Cocaine carboxylesterase) (Egasyn) (HMSE) (Methylumbelliferyl-acetate deacetylase 1) (EC 3.1.1.56) (Monocyte/macrophage serine estrase) (Retinyl ester hydrolase) (REH) (Serine esterase 1) (Triacylglycerol hydrolase) (TGH) | CES1 CES2 SES1 | *Homo sapiens* (Human) |

TABLE 3-continued

| | | Enzymes Classified as EC 3.1.1.1 | | |
|---|---|---|---|---|
| Entry | Entry name | Protein names | Gene Name | Organism |
| O46421 | EST1_MACFA | Liver carboxylesterase 1 | CES1 | *Macaca fascicularis* (Crab-eating macaque) (Cynomolgus monkey) |
| Q64419 | EST1_MESAU | Liver carboxylesterase | | *Mesocricetus auratus* (Golden hamster) |
| Q5RCL7 | EST3_PONAB | Carboxylesterase 3 (Liver carboxylesterase 31 homolog) | CES3 | *Pongo abelii* (Sumatran orangutan) (*Pongo pygmaeus abelii*) |
| P81429 | EST1_SCHGA | Esterase SG1 (Carboxylic-ester hydrolase) (Fragment) | SG1 | *Schizaphis graminum* (Green bug aphid) |
| Q47M62 | EST1_THEFY | Carboxylesterase | Tfu_2427 | *Thermobifida fusca* (strain YX) |
| Q64573 | EST4_RAT | Liver carboxylesterase 4 (Carboxyesterase ES-4) (Kidney microsomal carboxylesterase) (Microsomal palmitoyl-CoA hydrolase) | | *Rattus norvegicus* (Rat) |
| P25727 | EST5A_DROPS | Esterase-5A (Est-5A) (Carboxylic-eser hydrolase 5A) (Carboxylesterase-5A) | Est-5A Est5A GA23705 | *Drosophila pseudoobscura pseudoobscura* (Fruit fly) |
| Q8I034 | EST5A_FELCA | Carboxylesterase 5A (Carboxylesterase-like urinary excreted protein) (Cauxin) | CES5A CES7 | *Felis catus* (Cat) (*Felis silvestris catus*) |
| O00748 | EST2_HUMAN | Cocaine esterase (EC 3.1.1.84) Carboxylesterase 2) (CE-2) (hCE-2) (Methylumbelliferyl-acetate deacetylase 2) (EC 3.1.1.56) | CES2 ICE | *Homo sapiens* (Human) |
| Q3T930 | EST5A_SHEEP | Carboxylesterase 5A Carboxylesterase-like urinary excreted protein homolog) (Cauxin) Fragment) | CES5A CES7 | *Ovis aries* (Sheep) |
| O16170 | EST5B_DROMI | Esterase-5B (Est-5B) (Carboxylic-ester hydrolase 5B) (Carboxylesterase-5B) | Est-5B Est5B | *Drosophila miranda* (Fruit fly) |
| Q64176 | EST1E_MOUSE | Carboxylesterase 1E (Egasyn) (Liver carboxylesterase 22) (Es-22) (Esterase-22) | Ceste Es22 | *Mus musculus* (Mouse) |
| Q63108 | EST1E_RAT | Carboxylesterase 1E (Carboxyesterase ES-3) (ES-HTEL) (Egasyn) (Liver carboxylesterase 3) (pl 5.5 esterase) | Ces1e Ces1 | *Rattus norvegicus* (Rat) |
| P16854 | EST1_CULPI | Esterase B1 | B1 | *Culex pipiens* (House mosquito) |
| Q6UWW8 | EST3_HUMAN | Carboxylesterase 3 (Liver carboxylesterase 31 homolog) | CES3 UNQ869/PRO1887 | *Homo sapiens* (Human) |
| Q51758 | EST1_PSEFL | Carboxylesterase 1 (Esterase I) | estA | *Pseudomonas fluorescens* |
| P10094 | EST4_DROMO | Esterase-4 (Fragment) | Est-4 Est4 | *Drosophila mojavensis* (Fruit fly) |
| O16173 | EST5A_DROPE | Esterase-5A (Est-5A) (Carboxylic-ester hydrolase 5A) (Carboxylesterase-5A) | Est-5A Est5A | *Drosophila persimilis* (Fruit fly) |
| Q07085 | EST2_CAEEL | Esterase CM06B1 | F13H6.3 | *Caenorhabditis elegans* |
| Q6NT32 | EST5A_HUMAN | Carboxylesterase 5A (Carboxylesterase-like urinary excreted protein homolog) (Cauxin) | CES5A CES7 | *Homo sapiens* (Human) |
| Q5GRG2 | EST5A_RAT | Carboxylesterase 5A (Carboxylesterase-like urinary excreted protein homolog) (Cauxin) (Epididymis-specific gene 615 protein) | Ces5a Ces7 | *Rattus norvegicus* (Rat) |
| Q53547 | EST2_PSEFL | Carboxylesterase 2 (Esterase II) | estB | *Pseudomonas fluorescens* |
| O16171 | EST5C_DROPE | Esterase-5C (Est-5C) (Carboxylic-ester hydrolase 5C) (Carboxylesterase-5C) | Est-5C Est5C | *Drosophila persimilis* (Fruit fly) |
| P47982 | EST6_DROMA | Esterase 6 (Est-6) (Carboxylic-ester hydrolase 6) (Carboxylesterase-6) | Est-6 est6 | *Drosophila mauritiana* (Fruit fly) |
| Q08662 | EST6_DROSI | Esterase 6 (Est-6) (Carboxylic-ester hydrolase 6) (Carboxylesterase-6) | Est-6 est6 | *Drosophila simulans* (Fruit fly) |
| O33407 | ESTA_PSEAE | Esterase EstA (Autotransporter Esterase EstA) | estA papA PA5112 | *Pseudomonas aeruginosa* (strain ATCC 15692/DSM 22644/ CIP 104116/JCM 14847/ LMG 12228/1C/PRS 101/PAO1) |
| P81012 | ESTA_SCHGA | Esterase 52 kDa subunit (Carboxylic-ester hydrolase) (Fragment) | | *Schizaphis graminum* (Green bug aphid) |
| P81011 | ESTB_SCHGA | Esterase 56 kDa subunit (Carboxylic-ester hydrolase) (Fragment) | | *Schizaphis graminum* (Green bug aphid) |
| Q9WYH1 | ESTD_THEMA | Esterase EstD | estD TM_0336 THEMA_03040 Tmari_0334 | *Thermotoga maritima* (strain ATCC 43589/MSB8/ DSM 3109/JCM10099) |

TABLE 3-continued

<table>
<tr><td colspan="5" align="center">Enzymes Classified as EC 3.1.1.1</td></tr>
<tr><th>Entry</th><th>Entry name</th><th>Protein names</th><th>Gene Name</th><th>Organism</th></tr>
<tr><td>AKX74</td><td>ESTE_HVAVE</td><td>Putative esterase</td><td>ORF19</td><td><i>Heliothis virescens ascovirus</i> 3e (HvAV-3e)</td></tr>
<tr><td>P35501</td><td>ESTE_MYZPE</td><td>Esterase E4 (Carboxylic-ester hydrolase)</td><td></td><td><i>Myzus persicae</i> (Green peach aphid) (<i>Aphis persicae</i>)</td></tr>
<tr><td>Q0E588</td><td>ESTE_SFAVA</td><td>Putative esterase</td><td>ORF13</td><td><i>Spodoptera frugiperda ascovirus</i> 1a (SfAV-1a)</td></tr>
<tr><td>P18167</td><td>ESTP_DROME</td><td>Esterase P (Est-P) (Carboxylic-ester hydrolase P) (Carboxylesterase-P)</td><td>Est-P EstP CG17148</td><td><i>Drosophila melanogaster</i> (Fruit fly)</td></tr>
<tr><td>Q06174</td><td>EST_GEOSE</td><td>Carboxylesterase</td><td>est est30</td><td><i>Geobacillus stearothermophilus</i> (<i>Bacillus stearothermophilus</i>)</td></tr>
<tr><td>P23953</td><td>EST1C_MOUSE</td><td>Carboxylesterase 1C (Liver carboxylesterase N) (Lung surfactant convertase) (PES-N)</td><td>Ces1c Es1</td><td><i>Mus musculus</i> (Mouse)</td></tr>
<tr><td>P10959</td><td>EST1C_RAT</td><td>Carboxylesterase 1C (Carboxyesterase ES-1) (E1) (ES-THET) (Esterase-2) (Liver carboxylesterase 1) (Neutral retinyl ester hydrolase) (NREH) (Retinyl ester hydrolase) (REH)</td><td>Ces1c Es2</td><td><i>Rattus norvegicus</i> (Rat)</td></tr>
<tr><td>Q04456</td><td>EST1_CAEBR</td><td>Gut esterase 1 (Non-specific carboxylesterase)</td><td>ges-1 CBG06418</td><td><i>Caenorhabditis briggsae</i></td></tr>
<tr><td>Q04457</td><td>EST1_CAEEL</td><td>Gut esterase 1 (Non-specific carboxylesterase)</td><td>ges-1 R12A1.4</td><td><i>Caenorhabditis elegans</i></td></tr>
<tr><td>Q63880</td><td>EST3A_MOUSE</td><td>Carboxylesterase 3A (ES-male) (Liver carboxylesterase 31) (Esterase-31)</td><td>Ces3a Es31</td><td><i>Mus musculus</i> (Mouse)</td></tr>
<tr><td>Q8VCU1</td><td>EST3B_MOUSE</td><td>Carboxylesterase 3B (Liver carboxylesterase 31-like)</td><td>Ces3b Gm4738</td><td><i>Mus musculus</i> (Mouse)</td></tr>
<tr><td>Q8VCC2</td><td>EST1_MOUSE</td><td>Liver carboxylesterase 1 (Acyl-coenzyme A:cholesterol acyltransferase) (Carboxylesterase 1G) (ES-x)</td><td>Ces1 Ces1g</td><td><i>Mus musculus</i> (Mouse)</td></tr>
<tr><td>Q29550</td><td>EST1_PIG</td><td>Liver carboxylesterase (Proline-beta-naphthylamidase) (Retinyl ester hydrolase) (REH)</td><td></td><td><i>Sus scrofa</i> (Pig)</td></tr>
<tr><td>P12337</td><td>EST1_RABIT</td><td>Liver carboxylesterase 1 (Acyl-coenzyme A:cholesterol acyltransferase)</td><td></td><td><i>Oryctolagus cuniculus</i> (Rabbit)</td></tr>
<tr><td>P86325</td><td>EST1_THEFU</td><td>Carboxylesterase</td><td></td><td><i>Thermobifida fusca</i> (<i>Thermomonospora fusca</i>)</td></tr>
<tr><td>Q7AW47</td><td>EST5A_CANLF</td><td>Carboxylesterase 5A (Carboxylesterase-like urinary excreted protein homolog) (Cauxin)</td><td>CES5A CES7</td><td><i>Canis lupus familiaris</i> (Dog) (<i>Canis familiaris</i>)</td></tr>
<tr><td>O16168</td><td>EST5A_DROMI</td><td>Esterase-5A (Est-5A) (Carboxylic-ester hydrolase 5A) (Carboxylesterase-5A)</td><td>Est-5A Est5A</td><td><i>Drosophila miranda</i> (Fruit fly)</td></tr>
<tr><td>P21370</td><td>EST2_CUPLI</td><td>Esterase B2 (Fragment)</td><td></td><td><i>Culex pipiens</i> (House mosquito)</td></tr>
<tr><td>Q6AW46</td><td>EST5A_MOUSE</td><td>Carboxylesterase 5A (Carboxylesterase-like urinary excreted protein homolog) (Cauxin)</td><td>Ces5a Ces7</td><td><i>Mus musculus</i> (Mouse)</td></tr>
<tr><td>P14943</td><td>EST2_RABIT</td><td>Liver carboxylesterase 2</td><td>CES2 ICE</td><td><i>Oryctolagus cuniculus</i> (Rabbit)</td></tr>
<tr><td>O16172</td><td>EST5B_DROPE</td><td>Esterase-5B (Est-5B) (Carboxylic-ester hydrolase 5B) (Carboxylesterase-5B)</td><td>Est-5B Est5B</td><td><i>Drosophila persimilis</i> (Fruit fly)</td></tr>
<tr><td>P25726</td><td>EST5B_DROPS</td><td>Esterase-5B (Est-5B) (Carboxylic-ester hydrolase 5B) (Carboxylesterase-5B)</td><td>Est-5B Est5b GA14349</td><td><i>Drosophila pseudoobscura pseudoobscura</i> (Fruit fly)</td></tr>
<tr><td>O16169</td><td>EST5C_DROMI</td><td>Esterase-5C (Est-5C) (Carboxylic-ester hydrolase 5C) (Carboxylesterase-5C)</td><td>Est-5C Est5C</td><td><i>Drosophila miranda</i> (Fruit fly)</td></tr>
<tr><td>P25725</td><td>EST5C_DROPS</td><td>Esterase-5C (Est-5C) (Carboxylic-ester hydrolase 5C) (Carboxylesterase-5C)</td><td>Est-5C Est5C GA19955</td><td><i>Drosophila pseudoobscura pseudoobscura</i> (Fruit fly)</td></tr>
<tr><td>P10095</td><td>EST5_DROMO</td><td>Esterase-5 (Fragment)</td><td>Est-5 Est5</td><td><i>Drosophila mojavensis</i> (Fruit fly)</td></tr>
<tr><td>Q63010</td><td>EST5_RAT</td><td>Liver carboxylesterase B-1 (Liver microsomal carboxylesterase)</td><td></td><td><i>Rattus norvegicus</i> (Rat)</td></tr>
<tr><td>B2D0J5</td><td>EST6_APIME</td><td>Venom carboxylesterase-6 (allergen Api m 8)</td><td></td><td><i>Apis mellifera</i> (Honeybee)</td></tr>
<tr><td>P08171</td><td>EST6_DROME</td><td>Esterase-6 (Est-6) (Carboxylic-ester hydrolase 6) (Carboxylesterase-6)</td><td>Est-6 EST6 CG6917</td><td><i>Drosophila melanogaster</i> (Fruit fly)</td></tr>
<tr><td>Q6B6R8</td><td>ESTA_PSEPU</td><td>Esterase EstA</td><td>estA</td><td><i>Pseudomonas putida</i> (<i>Arthrobacter siderocapsulatus</i>)</td></tr>
<tr><td>P35502</td><td>ESTF_MYZPE</td><td>Esterase FE4 (Carboxylic-ester hydrolase)</td><td></td><td><i>Myzus persicae</i> (Green peach aphid) (<i>Aphis persicae</i>)</td></tr>
</table>

TABLE 3-continued

Enzymes Classified as EC 3.1.1.1

| Entry | Entry name | Protein names | Gene Name | Organism |
|---|---|---|---|---|
| Q88QS0 | ESTP_PSEPK | Esterase EstP (Autotransporter esterase EstP) (Palmitoyl-CoA hydrolase) (EC 3.1.2.2) | estP PP_0418 | *Pseudomonas putida* (strain ATCC 47054/DSM 6125/ NCIMB 11950/KT2440) |
| Q05487 | ESTS_DROVI | Esterase S (Est-S) (Carboxylic-ester hydrolase S) (Carboxylesterase-S) | EstS | *Drosophila virilis* (Fruit fly) |
| O32232 | EST_BACSU | Carboxylesterase | est yvaK BSU33620 | *Bacillus subtilis* (strain 168) |
| Q9HZY8 | EST_PSEAE | Esterase TesA | tesA PA2856 | *Pseudomonas aeruginosa* (strain ATCC 15692/DSM 22644/ CIP 104116/JCM 14847/ LMG 12228/1C/PRS 101/PAO1) |
| P9WK87 | NLHH_MYCTU | Carboxylesterase NlhH | nlhH lipH Rv1399c | *Mycobacterium tuberculosis* (strain ATCC 25618/H37Rv) |
| O06350 | LIPF_MYCTU | Carboxylesterase LipF | lipF Rv3487c | *Mycobacterium tuberculosis* (strain ATCC 25618/H37Rv) |
| L0TC47 | LIPV_MYCTU | Lipase LipV | lipV Rv3203 | *Mycobacterium tuberculosis* (strain ATCC 25618/H37Rv) |
| P9WK86 | NLHH_MYCTO | Carboxylesterase NlhH | nlhH lipH MT1443 | *Mycobacterium tuberculosis* (strain CDC 1551/Oshkosh) |
| P96688 | NAP_BACSU | Uncharacterized carboxylesterase nap | nap BSU05440 | *Bacillus subtilis* (strain 168) |

TABLE 4

Enzymes Classified as EC 3.1.1.7

| Entry | Entry name | Protein names | Gene Name | Organism |
|---|---|---|---|---|
| Q867X3 | ACES_CULPP | Acetylcholinesterase | ACE-1 | *Culex pipiens pipiens* (Northern house mosquito) |
| P04058 | ACES_TETCF | Acetylcholinesterase | Ache | *Tetronacrce californica* (Pacific electric ray) (*Torpedo californica*) |
| Q867X2 | ACES_CULQU | Acetylcholinesterase | ACE-1 | *Culex quinquefasciatus* (Southern house mosquito) (*Culex pungens*) |
| P38433 | ACE1_CAEEL | Acetylcholinesterase | ace-1 W09B12.1 | *Caenorhabditis elegans* |
| P21836 | ACES_MOUSE | Acetylcholinesterase | Ache | *Mus musculus* (Mouse) |
| P56161 | ACES_ANOST | Acetylcholinesterase | | *Anopheles stephensi* (Indo-Pakistan malaria mosquito) |
| P07140 | ACES_DROME | Acetylcholinesterase | Ace CG17907 | *Drosophila melanogaster* (Fruit fly) |
| O62763 | ACES_FELCA | Acetylcholinesterase | ACHE | *Felis catus* (Cat) (*Felis silvestris catus*) |
| P36196 | ACES_CHICK | Acetylcholinesterase | ACHE | *Gallus gallus* (Chicken) |
| Q92081 | ACES_MYXGL | Acetylcholinesterase | ache ace1 | *Myxine glutinosa* (Atlantic hagfish) |
| Q869C3 | ACES_ANOGA | Acetylcholinesterase | Ace ACE1, ACHE1, AGAP001356 | *Anopheles gambiae* (African malaria mosquito) |
| Q27459 | ACES_CAEBR | Acetylcholinesterase 1 | ace-1 CBG16374 | *Caenorhabditis briggsae* |
| O42275 | ACES_ELEEL | Acetylcholinesterase | Ache | *Electrophorus electricus* (Electric eel) (*Gymnotus electricus*) |
| P07692 | ACES_TORMA | Acetylcholinesterase | Ache | *Torpedo marmorata* (Marbled electric ray) |
| P23795 | ACES_BOVIN | Acetylcholinesterase | ACHE | *Bos taurus* (Bovine) |
| Q86GC8 | ACES_CULPI | Acetylcholinesterase | ACHE1 | *Culex pipiens* (House mosquito) |
| Q27677 | ACES_LEPDE | Acetylcholinesterase | | *Leptinotarsa decemlineata* (Colorado potato beetle) (*Doryphora decemlineata*) |
| P37136 | ACES_RAT | Acetylcholinesterase | Ache | *Rattus norvegicus* (Rat) |
| Q86GC9 | ACES_CULTO | Acetylcholinesterase | ACE-1 | *Culex torrentium* (Mosquito) |
| W4VSJ0 | ACES_TRILK | Acetylcholinesterase-1 | | *Trittame loki* (Brush-footed trapdoor spider) |
| Q9DDE3 | ACES_DANRE | Acetylcholinesterase | Ache | *Danio rerio* (Zebrafish) (*Brachydanio rerio*) |
| P22303 | ACES_HUMAN | Acetylcholinesterase | ACHE | *Homo sapiens* (Human) |
| Q7LZG1 | ACES_NAJOX | Acetylcholinesterase | ACHE | *Naja oxiana* (Central Asian cobra) (*Oxus cobra*) |
| Q9NDG8 | ACE4_CAEBR | Acetylcholinesterase | ace-4 CBG02827 | *Caenorhabditis briggsae* |
| Q29499 | ACES_RABIT | Acetylcholinesterase | ACHE | *Oryctolagus cuniculus* (Rabbit) |
| Q92035 | ACES_BUNFA | Acetylcholinesterase | ACHE | *Bungarus fasciatus* (Banded krait) (*Pseudoboa fasciata*) |

TABLE 5

Mutations in *Lucilia cuprina*

| Mutation | Comments | Literature |
|---|---|---|
| E217M | mutant in anionic site, p1 subsite, pyrethroid hydrolysis similar to wild-type | 668944 |
| F309L | mutatn in acyl pocket p2 subsite, marked increase in pyrethroid hydrolysis both for cis-substrate, strong increase for trans-substrate | 668944 |
| F354L | mutant in anionic site, p1 subsite, pyrethroid hydrolysis similar to wild-type | 668944 |
| F354W | mutant in anionic site, p1 subsite, marked increase in pyrethroid hydrolysis both for cis-and trans-substrate | 668944 |
| G137D | mutant in oxyanion hole, marked decrease in pyrethroid hydrolysis | 668944 |
| G137E | mutant in oxyanion hole, strong decrease in pyrethroid hydrolysis | 668944 |
| G137H | mutant in oxyanion hole, marked decrease in pyrethroid hydrolysis | 668944 |
| G137R | mutant in oxyanion hole, pyrethroid hydrolysis similar to wild-type | 668944 |
| M364L/I419F/A472T/ I505T/K530E/D554G | the mutant shows enhanced activity | 730817 |
| W251A | mutant in acyl pocket p2 subsite, marked in create in pyrethroid hydrolysis both for cis-and trans-substrate | 668944 |
| W251G | mutant in acyl pocket p2 subsite, marked in create in pyrethroid hydrolysis both for cis-and trans-substrate | 668944 |
| W251L | mutant in acyl pocket p2 subsite, strong increase in pyrethroid hydrolysis both for cis-and trans-substate. Trans:cis ratio for preference of substrate is 2:1 compared to 27:1 in wild-type | 668944 |
| W251L/D449G | the mutant shows a loss of activity for most substrates | 729826 |
| W251L/D473N | the mutant shows a loss of activity for most substrates | 729826 |
| W251L/F309L | mutant in acyl pocket p2 subsite, strong increase in pyrethroid hydrolysis both for cis-and trans-substate. Trans:cis ratio for preference of substrate is 2:1 compared to 27:1 in wild-type | 668944 |
| W251L/G137D | mutant in acyl pocket p2 subsite, strong increase in pyrethroid hydrolysis both for cis-and trans-substate. Trans:cis ratio for preference of substrate is 2:1 compared to 27:1 in wild-type | 668944 |
| W251L/I140F | the mutant shows a loss of activity for most substrates | 729826 |
| W251L/I459N | the mutant shows a loss of activity for most substrates | 729826 |
| W251L/P250S | mutant in acyl pocket p2 subsite, strong increase in pyrethroid hydrolysis both for cis-and trans-substate. Trans:cis ratio for preference of substrate is 2:1 compared to 27:1 in wild-type | 668944 |
| W251L/R458C | the mutant shows a loss of activity for most substrates | 729826 |
| W251L/R461H | the mutant shows a loss of activity for most substrates | 729826 |

As described herein, the conversion of the second substrate by the second enzyme results in basification of the reaction buffer. Representative examples of a second substrate and second enzyme include, but are not limited to urea and urease (classified as EC 3.5.1.5), urea and urea amidolyase (classified as EC 6.3.4.6 and EC 3.5.1.54), biuret and biuret amidohydrolase (classified as EC 3.5.1.84), [beta-hydroxypyruvate+glycolaldehyde] and transketolase (classified as EC 2.2.1.1, with representative examples of substrates being: D-fructose 6-phosphate, D-glyceraldehyde 3-phosphate, D-ribose 5-phosphate, or D-xylulose 5-phosphate), adenosine and adenosine deaminase (classified as EC3.5.4.4), adenine and adenine deaminase (classified as EC 3.5.4.15), guanosine and guanosine deaminase (classified as EC 3.5.4.15), guanine and guanine deaminase (classified as EC 3.5.4.3), cytosine and cytosine deaminase (classified as EC 3.5.4.5).

Moreover, representative second enzyme/second substrate combinations can be selected from those shown in Table 6.

In preferred embodiments, ureases are used as the second enzyme. Ureases (EC 3.5.1.5) are highly homologous nickel-dependent enzymes widespread among plants, bacteria and fungi, that hydrolyse urea into ammonia and carbon dioxide [1, 2]. Plant and fungal ureases are homotrimers or hexamers of a ~90 kD subunit, while bacterial ureases are multimers of two or three subunits complexes [3-4]. The N-terminal halves of plant or fungal urease single chain align with the primary sequence of the small subunits of most bacterial enzymes (e.g.p and y chains of *Bacillus pasteurii* urease or the A subunit of *Helicobacter pylori* urease). The C-terminal portions of plant and fungal chains resemble the large subunits of bacterial ureases (e.g.a chain of *B. pasteurii* urease or the B subunit of *H. pylori* enzyme). Considering the similarity in their sequences, all ureases are likely to possess similar tertiary structures and catalytic mechanisms indicating they are variants of the same ancestral protein [2]. *H. pylori* urease (1E9Z) and jackbean (Canavalia *ensiformis*) major urease (P07374), share about 50% identity despite differences in their quaternary structures. The 3D crystallographic structures of three bacterial ureases were successfully resolved: *Klebsiella aerogenes* (1FWJ), *B. pasteurii* (4UBP) and *H. pylori* (1E9Z).

TABLE 6

| Enzyme | substrate | Reaction products | Enzyme class | Reference(s) | Seq-ID examples |
|---|---|---|---|---|---|
| urease | urea | $CO_2$ + 2 $NH_3$ | 3.5.1.5 | Balasubramanian 2010; Wassermann 2010; Kappaun 2018; Filiz 2016 | P07374, I1K3K3, 1FWJ, 4UBP, 1E9Z |
| allophanate hydrolase | Allphanate [1] | $CO_2$ + 2 $NH_3$ | 3.5.1.54 | Zhao 2018 | Q936X2, 4CP8 |

TABLE 6-continued

| Enzyme | substrate | Reaction products | Enzyme class | Reference(s) | Seq-ID examples |
|---|---|---|---|---|---|
| Urea amidolyase | Urea + ATP + $HCO_3^-$ | $2 CO_2 + 2 NH_3$ | 6.3.4.6 + 3.5.1.54 | Zhao 2018 | |
| Biuret amidohydrolase | biuret | urea + $CO_2$ + $NH_3$ | 3.5.1.84 | Esquirol 2018 | A0A075T5U3, Q1M7F4 |
| Transketolase | β-hydroxypyruvate + glycolaldehyde | L-erythrulose + $CO_2$ | 2.2.1.1 | Gruber 2017 | |
| Adenosine deaminase | Adenosine | Inosine + $NH_3$ | 3.5.4.4 | Alberty 2007 | P00813, P22333, |
| Adenine deaminase | Adenine | Hypoxanthine + $NH_3$ | 3.5.4.2 | | |
| Guanosine deaminase | Guanosine | Xanthosine + $NH_3$ | 3.5.4.15 | | P76641 |
| Guanine deaminase (Cypin) | Guanine | Xanthine + $NH_3$ | 3.5.4.3 | Bitra 2013a, Bitra2 013b | Q82Y41 |
| Cytidine deaminase | Cytidine | Uridine + $NH_3$ | 3.5.4.5 | Dong 2015 | P0ABF6 |

Ph changes can be measured using standard techniques known in the art. For example, techniques such as described in Gruber et al., "Real-time pH monitoring of industrially relevant enzymatic reactions in a microfluidic side-entry reactor (pSER) shows potential for pH control" Biotechnology Journal, Vol. 12:6 (June 2017) can be used. In this example, enzyme activity was determined by mixing 250 μL of a 100 mM lithium-p-hydroxypyruvate (HPA) and 100 mM glycolaldehyde (GA) solution with 250 μL of a trans-ketolase lysate solution (250 μL of TK lysate, 4.8 mM thiamine diphosphate ThDP and 19.6 mM magnesium chloride $MgCl_2$). Both solutions were prepared in 50 mM Tris-HCl buffer pH 7.0.

In another example, biuret hydrolase can also be used to measure pH change as described in Esquirol et al. "Structural and biochemical characterization of the biuret hydrolase (BiuH) from the cyanuric acid catabolism pathway of *Rhizobium leguminasorum* bv. *viciae* 3841" PLOS/ONE (2018). Here Biuret hydrolase specific activity was obtained by using 22 nM of biuret hydrolase wild type or 0.22 μM of the variants and 5 mU/μL of GDH in presence of 1.2 mM of biuret in 25 mM potassium phosphate buffer pH 8.5, at 28° C. Biuret hydrolase kinetic data were measured for the wild type and all the variants having a residual specific activity above 1% of the wild type enzymes, by using 22 nM of biuret hydrolase enzyme and either 2.9 μM or 0.9 μM of the variants, depending on their performance in presence of various concentrations of biuret ranging from 0-4 mM, using the GDH-coupled assay. All the kinetics constants were calculated using GraphPad Prism (GraphPad Software, San Diego, USA) fitting the rate data to the Michaelis-Menten equation.

D. Device Used to Detect Phosphorothionate "Thion" Forms of OP

However, unlike OP nerve agents, which are potent inhibitors in their native non-activated forms, certain phosphorothionate insecticides such as chlorpyrifos, malathion and parathion must first be converted to replace the P=S bond with a P=O bond, e.g. by P450 to generate the active oxon form (e.g., chlorpyrifos oxon (CPO), malathion oxon (MX) and paraoxon (PX)) for their insecticidal action. Moreover, the $k_i$ values obtained for AChE by oxons (e.g., CPO, MO, PX) are 10-fold to 100-fold lower than nerve agents (~$1.0 \times 10^7$ $M^{-1} \cdot min^{-1}$) while the unmodified forms (e.g., malathion) is up to 1,000-fold lower. This translates into a very slow yellow to pink (Y-P) color change and requires modification in the OP/C Detecting Enzyme (amount and activity) in the first carrier material of the device to convert the thion to the oxon form in order to enhance the rate of reaction and produce an efficient device as described herein.

Thus, to detect certain OP/C insecticides, the device needs to further comprise the ability to convert a thion form of the OP to the oxon form.

Another approach in obtaining satisfactorily low inhibition constants (e.g., a ki in the range of $10^5$-$10^6$ M–1·min–1) includes producing and incorporating the P450 (such as for example, (CYP1A2, CYP6G1) along with cytochrome c reductase (NAPDH) into the first carrier material, ampoule or second carrier material to enzymatically convert the OP/C pesticide thion to the oxon forms. For example, OPs with sufficient inhibition of the OP/C Detecting Enzyme (e.g. ki=$10^5$ $M^{-1} \cdot min^{-1}$), can be immediately used in the device. However, OP/C having low inhibition (e.g. ki=$10^{1-3}$ $M^{-1} \cdot min^{-1}$, such as in the case of the thion forms of OP/C insecticides) will need conversion to the oxon forms either chemically (e.g., by chemical oxidizers such as for example halogens (e.g., fluorine, chlorine, bromine and iodine) or by the P450 (plus NADPH). FIG. 8 shows the structure of the most commonly used OP/C insecticides in Asia, Central America, India and the USA and how the ($ki^{high}$) already containing the P=O bond and thus highly toxic, represent some of the most widely used toxic OP/C insecticides in these regions (Table 7). Thus, it is anticipated that food samples, for example, from these regions can be quickly tested for the presence of OP/C pesticides when then device converts the thion form to oxon forms.

TABLE 7

| Some of the most commonly used OP insecticides used in each country. | | | | |
|---|---|---|---|---|
| United States | Mexico | China | India | Thailand |
| Chlorpyrifos | Chlorpyrifos | Dichlorvos* | Monocrotophos* | Chlorpyrifos |
| Acephate* | Omethoate* | Methamidophos* | Triazophos | Malathion |
| Malathion | Dimethoate* | Omethoate* | Phosphamidon | Monocrotophos* |
| Naled | Acephate* | Acephate | Methyl parathion | Diazinon |
| Phorate | Triazophos | Dimethoate | Phorate | Omethoate* |
| Dicrotophos* | Methyl Parathion | Isocarbophos | | Dicrotophos* |
| Phosmet | Monocrotophos* | | | Methyl Parathion |
| Dimethoate | Phorate | | | |
| Terbufos | Milk# | | | |
| Ethoprophos | Dichlorvos* | | | |
| Tetrachlorvinphos | Phorate | | | |
| | Chlorpyrifos, | | | |
| | chlorfenvinphos | | | |

The insecticides are listed as to usage (tonnes) where it is known. Many of these insecticides are used despite ban in many countries. Many other less used insecticides are not listed.

Toxic ki$^{high}$ insecticides against CES tested to date.

\# Widely used as dairy cattle ectoparasiticides or in crops used for animal feed, in homogenized and pasteurized Mexican milk samples.

For example, by using a P450 enzyme along with the co-factor NAPDH, the efficiency of the enzymatic conversion of the substrate by the OP/C Detecting Enzyme is improved, thereby increasing the ability to detect OPs having high kl. Representative P450 proteins that can be used include but are not limited to example of P450 enzyme is a triple mutant of CYP1A2 (P450 BM-3 (CYP102-A1). The P450/NAPDH can be included on the second carrier material, within the ampoule or included within the first carrier material. Expression of P450 CYP6G1 in plants has been described and thus we intend to explore in-house production in plants. In addition, several commercial recombinant cytochrome P450/NADPH reagents, both human (CYP1A2 (Sigma #C8113 made in Baculovirus-infected insect cells; #E9288 expressed in *Saccharomyces cerevisiae*) and insects (CYP6G1 kindly provided by Dr. Colin Jackson, ANU, Australia) are available and will also be tested. Also, cytochrome P450 (CYP1A2)/NADPH microsomes (Fischer Scientific) are available and were used in FIG. 1b.

EXAMPLES

The invention will now be further illustrated with reference to the following examples. It will be appreciated that what follows is by way of example only and that modifications to detail may be made while still falling within the scope of the invention.

Example 1. Production of Plant-Derived CES Extract or Purified Protein

Representative OP/C Detecting Enzymes, human carboxylase CES1 and CES 2, was produced in leaf extract as described below. Constructs were engineered using methods and strategies described previously. See, Rosenberg, Y. J. et al. "A Highly Stable Minimally Processed Plant-Derived Recombinant Acetylcholinesterase For Nerve Agent Detection In Adverse Conditions," Sci. Rep. 5, 13247; doi: 10.1038/srep13247 (2015).

*Homo sapiens* Carboxylesterase 1
GenBank: BC012418.1)(/protein_id="AAH12418.1)
Has 1). K78:E183 and K275:E292 salt bridges (yellow)
2). C87-C116 & C274-C285 disulphide bridges (green)
3). N79Q, S221A mutation not resent blue >hCES1

(SEQ ID NO: 5)

MWLPALVLATLAASAAWGHPSSPPVVDTVHGKVLGKFVSLEGFAQP

VAIFLGIPFAKPPLGPLRFTPPQPAEPWSFVKNATSYPPMCTQDPKAGQ

LLSELFTNRKENIPLKLSEDCLYLNIYTPADLTKKNRLPVMVWIHGGGL

MVGAASTYDGLALAAHENVVVVTIQYRLGIWGFFSTGDEHSRGNWGHLD

QVAALRWVQDNIASFGGNPGSVTIFGESAGGESVSVLVLSPLAKNLFHR

AISESGVALTSVLVKKGDVKPLAEQIAITAGCKTTTSAVMVHCLRQKTE

EELLETTLKMKFLSLDLQGDPRESQPLLGTVIDGMLLLKTPEELQAERN

FHTVPYMVGINKQEFGWLIPMLMSYPLSEGOLDQKTAMSLLWKSYPLVC

IAKELIPEATEKYLGGTDDTVKKKDLFLDLIADVMFGVPSVIVARNHRD

AGAPTYMYEFQYRPSFSSDMKPKTVIGDHGDELFSVFGAPFLKEGASEE

EIRLSKMVMKFWANFARNGNPNGEGLPHWPEYNQKEGYLQIGANTQAAQ

KLKDKEVAFWTNLFAKKAVEKPPQTTEHIEL

>hCES2 (ACCESSION U60553)
MSAVACGLLLLLVRGQGQDSASPIRTTHTGQVLGSLVHVKGANAGVQTF

LGIPFAKPPLGPLRFAPPEPPESWSGVRDGITHPAMCLQDLTAVESEFL

SQFNMTFPSDSMSEDCLYLSIYTPAHSHEGSNLPVMVWIHGGALVFGMA

SLYDGSMLAALENVVVVIIQYRLGVLGFFSIGDKHATGNWGYLDQVAAL

RWVQQNIAHFGGNPDRVTIFGESAGGTSVSSLVVSPISQGLFHGAIMES

GVALLPGLIASSADVISTVVANLSACDQVDSEALVGCLRGKSKEEILAI

NKPFKMIPGVVDGVFLPRHPQELLASADFQPVPSIVGVNNNEFGWLIPK

VMRIYDTQKEMDREASQAALQKMLILLMLPPTFGDLLREEYIGDNGDPQ

TLQAQFQEMMADSMFVIPALQVAHFQCSRAPVYFYEFQHQPSWLKNIRP

PHMKADHGDELPFVERSFFGGNYIKFTEEEEQLSRKMMKYWANFARNGN

PNGEGLPHWPLFDQEEQYLQLNLQPAVGRALKAHRLQFWKKALPQKIQE

LEEPEERHTEL

Additionally, OP/C Detecting Enzyme constructs comprising human AChE and/or BChE were generated as described previously in US2017/0081649, which is herein incorporated by reference in its entirety. Production of any of the enzymes can be performed as follows.

One liter of a modified extraction buffer containing 5 mM $MgCl_2$, 4 mM DTT, 150 mM sodium metabisulfite and 10% sucrose in PBS pH 7.4 was prepared and chilled at 4° C. before use. Chitosan was prepared (Chitosan, low molecular weight, Sigma Aldrich 448869-50 g) by adding 1% w/v chitosan into 1% acetic acid and the solution stirred for at least 30 minutes until dissolved and taking on a gelatinous looking appearance. Frozen leaves were ground in a Vitamix blender with 5× w/v extraction buffer. After grinding, the slurry was passed through Miracloth (Calbiochem #475855), poured into centrifuge bottles and centrifuged at 20,000×g for 15 minutes. After centrifugation, the supernatant was poured into a beaker, pH changed to 7.4 and chitosan added at 0.2% v/v. The extract containing chitosan was then stirred at 4° C. for 30 minutes, removed from the stirrer, and left for an additional 30 minutes at 4° C. The extract was poured into centrifuge bottles and centrifuged at 1500 rpm in a refrigerated Sorvall RT6000 at 4° C. for 5 minutes. Supernatant was decanted and left at 4° C. until enzyme level was determined. In some cases, collagen hydrolysate was added to the extract prior to it being aliquoted and frozen at −20° C.

The rHuCES1 was expressed and the extract and purified essentially as described previously for AChE (Rosenberg 2015). Briefly, the C-terminally His-tagged rHuCES1 was expressed by in N. b benthamiana using the Agrobacterium leaf infiltration method and extracted from the leaves using a blender and 5 mL of extraction buffer per gram of leaf biomass. The homogenate was filtered through miracloth, clarified by centrifugation and the pH adjusted to 7.4 before adding chitosan to precipitate phenols, fatty compounds and other impurities. After a second centrifugation step the pH was adjusted to 8.0 and DEAE Sephadex A-25 was added to remove further contaminants by negative ion exchange batch chromatography. The supernatant was 0.45 μm filtered, pH re-adjusted to 8.0, centrifuged and loaded onto a $Ni^{2+}$-NTA resin. Bound proteins were eluted by step gradients of 30 mM and 100 mM imidazole and elution fractions tested for enzyme activity. Positive fractions were pooled, concentrated by ultrafiltration, dialyzed against 10 mM Tris pH 8.0 and stored at 4° C.

OP/C Detecting Enzyme activity can be determined spectrophotometrically at 25° C. according to the Ellman method. See Ellman et al., 1961, which is herein incorporated by reference. For example, to assess AChE activity, the assay mixture contains 1 mM aceylthiocholine as the substrate and 1 mM 5,5-dithiobisnitrobenzoic acid (DTNB) in 50 mM sodium phosphate, pH 8.0. at room temperature (RT). In assays using mammalian cells, 20 uM ethopropazine is used as a BChE-specific inhibitor. BChE activity was assessed similarly using 1 mM butyrylthiocholine (BTC) as an example as substrate and 0.5 mM 5,5-dithiobis 2-nitrobenzoic acid (DTNB), The was followed by monitoring the increase in absorbance of 5-thio-2-nitrobenzoic acid at 412 nm using a molar extinction coefficient of 14,150 $M^{-1} cm^{-1}$. One unit of the enzyme activity is defined as the amount required to hydrolyze 1 μmol of substrate/min.

Carboxylesterase activity can be assessed was determined by conversion of 4-Nitrophenyl acetate and determination of the liberated 4-Nitrophenyl by absorbance at 405 nm. Buffer was used as negative control. Kinetic measurements and Vmax determination were performed on a Spectramax plus 384 microplate reader (Molecular Devices) using Softmax Pro. Several alternative substrates are readily available and will be analyzed for increased turnover rates. Previous studies showed that 4-nitrophenyl-butyrate is the best substrate for HuCES2 among several 4-nitrophenyl esters [31, 33].

Alternatively, the OP/C Detecting Enzyme can be readily produced using a transient N. benthamiana plant expression system which is inexpensive and can produce kilogram amounts of extract in <2 weeks. See, for example U.S. Pat. No. 10,221,402 which is hereby incorporated by reference in its entirety. Specifically, transient plant expression can generate extracts that contain sufficient OP/C Detecting Enzyme activity and purification was not needed for purposes of detection of OPs in the device. Recombinant enzymes in supernatants (SN) or extracts can be purified using procainamide sepharose chromatography as described previously (De la Hoz et al., 1986). After loading the SN or extract and washing the column, BChE is generally eluted with a 0.1-1 M NaCl gradient but both AChE and BChE can be efficiently eluted using either 0.2 M procainamide, 0.2 M acetylcholine, 0.02 M decamethodium, 0.5 M chlorine chloride or 0.5 M tetra methyl ammonium bromide.

Besides plant expression, a variety of host-expression vector systems may also be utilized to express OP/C Detecting Enzyme. Such host-expression systems represent vehicles by which the coding sequences of interest may be produced and subsequently purified, but also represent cells which may, when transformed or transfected, with the appropriate nucleotide coding sequences, express the OP/C Detecting Enzyme. These include, but are not limited to, microorganisms such as bacteria (e.g., E. coli, B. subtilis) transformed with recombinant bacteriophage DNA, plasmid DNA or cosmid DNA expression vectors containing sequences; yeast (e.g., Saccharomyces, Pichia) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, are used for the expression of the OP/C Detecting Enzyme. For example, mammalian cells such as Chinese hamster ovary cells (CHO), in conjunction with a vector such as the major intermediate early gene promoter element from human cytomegalovirus is an effective expression system (Foecking et al., Gene 45:101 (1986); Cockett et al., Bio/Technology 8:2 (1990)).

In bacterial systems, a number of expression vectors may be advantageously selected depending upon the intended use. For example, when a large quantity of a protein is to be produced, vectors which direct the expression of high levels of OP/C Detecting Enzyme that are readily purified may be desirable. Such vectors include, but are not limited to, the E. coli expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109

(1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or Factor Xa protease cleavage sites so that the cloned target gene product (e.g., OP/C Detecting Enzyme) can be released from the GST moiety.

In an insect system, *Autographa californica* nuclear polyhedrosis virus (AcNPV) may be used as a vector to express an OP/C Detecting Enzyme. The virus grows in *Spodoptera frugiperda* cells. Coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized express the OP/C Detecting Enzyme. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination.

Insertion in a non-essential region of the viral genome (e.g., region El or E3) will result in a recombinant virus that is viable and capable of expressing the OP/C Detecting Enzyme in infected hosts (e.g., see Logan & Shenk, Proc. Natl. Acad. Sci. USA 8 1:355-359 (1984)).

Example 2. Bimolecular Rate Constants (Ki) of AChE Inhibition of CES and rHuAChE by Thion and Oxon Forms of OP Insecticides While the ki for rHuAChE for nerve agents is high (~$10^8$ $M^{-1} \cdot min^{-1}$), the inhibition constants (ki) of rHuAChE for selected OP insecticides (dichlorvos, chlorpyrifos and malathion) (paraoxon control) were found to be 10-1,000 lower than that for OP nerve agents. By comparison, carboxylesterase (CES) exhibits 10-1,000 higher inhibition parameters for both the thion and oxon forms of pesticides than rHuAChE. Thus, in preferred embodiments, HuCES can be used in the device as described herein.

For example, previously published results have shown that the Australian blow fly *Lucilia cuprina* carboxylesterase (LcαE7) has a high affinity (~5 μM) and kinetic parameters (~$1.0 \times 10^7$ $M^{-1} \cdot min^{-1}$) for a thion form of OP insecticide (17) and that the αE7 mutant form (LcαE7G137D) had an increased rate of turnover by two orders of magnitudes for paraoxon hydrolysis. Based on these data, we propose to include these OP/C Detecting Enzymes in the device as described herein.

Figure 1B:
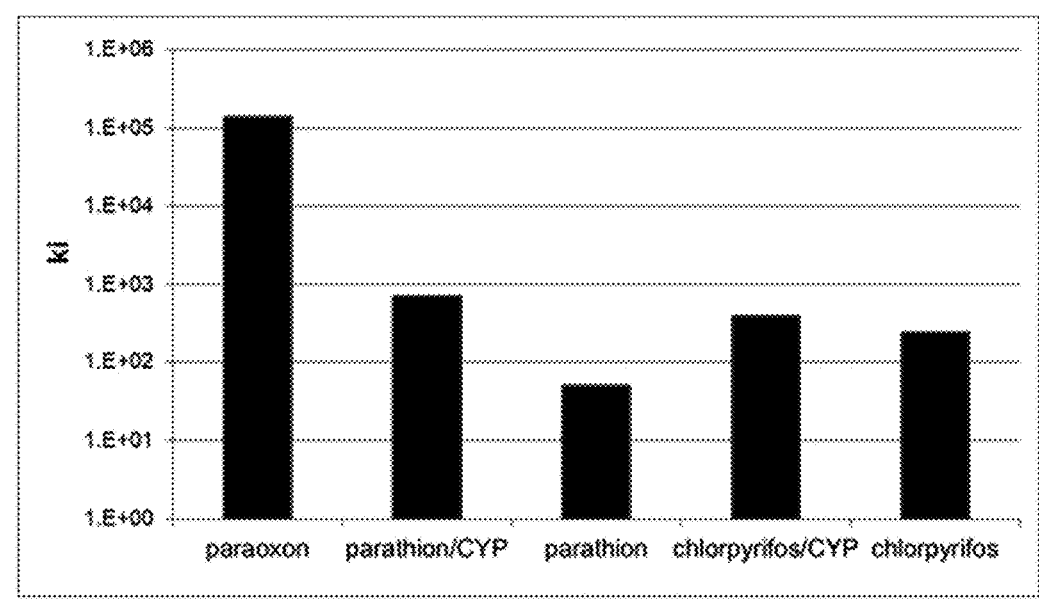
FIG. 1B shows the in vitro conversion of parathion to paraoxon using cytochrome P450 (CYP1A2)/NADPH microsomes (Fisher Scientific).

Specifically, the human carboxylesterase 1 (CES1) gene (GenBank Accession #AAH12418.1) and the CES2 gene (GenBank Accession #AAB03611.1) are produced transiently in *N. bentiamiana* as described above. Two forms with and without N-terminal His tags were compared and purified: the former giving better yields in preliminary studies. The plant-derived rHuCE extracts were tested against a battery of OP insecticides. Results showing different levels of plant rHuCE inhibition by different oxon and thion forms of OP insecticides are shown in FIG. 1A.

While certain OP insecticides had sufficiently high ki against rHuCE to elicit a rapid color change in a PESTpen (~$10^5$ $M^{-1} \cdot min^{-1}$), values of many others e.g., parathion, omethoate, malathion, chlorpyrifos, daizonin, etc. were only $10^{1-3}$ $M^{-1} \cdot min^{-1}$, and needed to undergo oxidation to convert the thion form to an oxon. In a preliminary in vitro study, the addition of an oxidizer, such as for example, CYPP450/NADPH microsomes (Fischer) increased the ki of parathion 10-fold while chlorpyrifos increased only slightly. See FIG. 1B. These early data demonstrate that thion conversion can be optimized using an oxidizer such as P450/NADPH.

In fact, when this experiment was repeated, a greater than 50-fold increase was observed. Here, 25 and 50 ul cytochrome P450 (CYP1A2) (Fischer Scientific and Sigma Aldrich) plus NADPH (1 mM) were added to 58 ug of parathion and 70 ug of chlorpyrifos, incubated for 10, 20 and 40 mins, and serially diluted prior to the addition of rHuCES for an additional 10 mins. FIG. 1D shows 50-fold increases in the ki of parathion and 20-fold for chlorpyrifos after 10 mins incubation with P450 with clear positives at 5.8 and 7 ug respectively. No differences were observed when preincubation of OP with P450 was extended to 20 and 40 mins and only small differences were seen using 25 vs 50 ul P450.

Figure 1C:
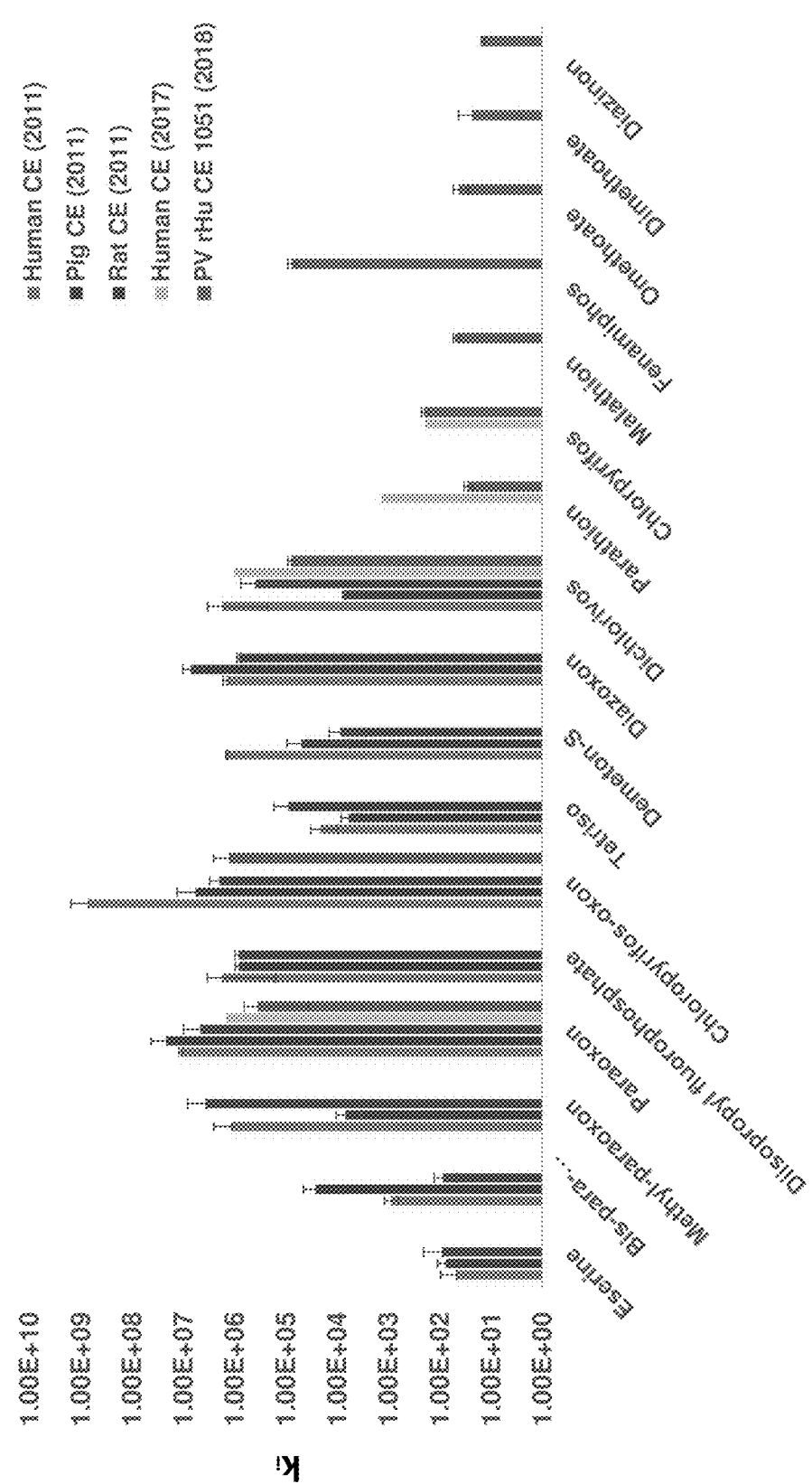
FIG. 1C shows the bi-molecular rate constants of the plant-derived rHuCE extracts against a battery of OP insecticides as compared to the purified rHuCE controls produced in E. coli.

FIG. 1C indicates that the bi-molecular rate constants of the plant-derived rHuCE extracts against a battery of OP insecticides were similar to the purified in-house rHuCE controls produced in *E. coli*. FIG. 1C also shows that the OP insecticides fell into two groups; those with low ki ($10^1$-$10^3$ $M^{-1} \cdot min^{-1}$) versus those with high ki ($10^5$ $M^{-1} \cdot min^{-1}$). This was shown to correlate with their structure in that insecticides e.g. malathion, parathion, chlorpyrifos exhibiting low ki had P=S bonds and required desulfuration for their phosphorylating activity, while dichlorvos, fenamiphos and methamidophos already had a P=O bond and already active.

Example 3: Device Capable of Detecting OPs

In preferred embodiments, the enzymatic components, including the recombinant OP/C Detecting Enzymes produced in Example 1 will be manufactured together with an applicator first carrier material, such as for example a polyurethane foam applicator sponge, while the first substrate and other additives (tinting compounds, surfactants, rheological thickeners and enzyme substrates) are kept in one reservoir, i.e. second carrier material and buffers in a second reservoir, i.e. the ampoule.

For example, in one embodiment, rHuCE will be embedded in the first carrier material (preferably a polyurethane foam) in the device described herein. The bottom piece (130) of the device contains dried chemistries and a glass ampoule (120) full of aqueous buffer. The user cracks the ampoule to activate the device, then inverts the device and turns the barrel to introduce the wet chemistry to the enzymatic foam. Once activated, the cap can then be removed and the first carrier material (100) can be used to sample surfaces.

In further details, an OP/C Detecting Enzyme, such as for example CES, can be co-immobilized on the first carrier material with nitrazine yellow dye. The first carrier material (150 mg disks) can be incubated (2 ml) with various concentrations of dimethyl methylphosphonate (DMMP), for thirty minutes, A concentrated solution (2 ml) of the first substrate (i.e., 50 mM of a 4-nitrophenyl ester) can then be applied to each first carrier material by breaking of the ampoule. As CES catalyzes the first substrate hydrolysis, the pH is reduced, and the first carrier material underwent a transition from bluish-brown to orange. However, it the first carrier material comes in contact with an OP/C, the conversion of the first substrate to acetic acid is inhibited and the color change occurs.

Once a surface is sampled, the cap can then be replaced, and the colorimetric scheme (yellow to red) reports on whether there are any OPs present within two to 20 minutes (FIG. 2*d*-4). In preferred embodiments, the enzyme shelf-life times for the products in device must exceed 60 days when incubated at 37° C.

In certain embodiments, both a minimally processed OP/C Detecting Enzyme (including but not limited to a plant extract) as well as purified protein can be used in the first carrier material for optimal costs savings.

Example 4: Device Capable of Detecting Thion OPs and/or OPs with Low Ki

As noted, in insects and mammals, cytochrome c P450 in the liver (in the presence of NADPH converts OPs from the thion form to the oxon form. In preliminary studies (FIGS. 1B and 1D) a 10-fold, and even a 50-fold, increase in ki of rHuCE against parathion was achieved in vitro. These chemical oxidizers are much more powerful than P450 and should more rapidly convert the thions to oxons and this increase the speed of OP/C detection. Likewise, the P450 assay can be optimized in the same manner to optimize the oxidation conditions.

For chemical oxidation, it has been demonstrated that oxidation by iodine or Fenton's reagent catalysts readily converts parathion into paraoxon; with readily increased toxicity in AChE-based assays. This same strategy can readily be optimized in vitro and translated into the device form factor to rapidly demonstrate the capability with rHuCE. Such chemicals may be more powerful than P450 and may greatly increase the reaction rate and color change in a device The reference to any prior art in this specification is not, and should not be taken as, an acknowledgement of any form of suggestion that such prior art forms part of the common general knowledge.

It will be appreciated that the disclosure is not limited to the embodiment or embodiments disclosed, but is capable of numerous rearrangements, modifications and substitutions without departing from the scope of the disclosure as set forth and defined by the following claims. The entire teachings of any patents, patent applications or other publications referred to herein are incorporated by reference herein as if fully set forth herein.

---

What is claimed:

1. A device for detecting an organophosphate (OP) and carbamate (C) "OP/C" compound comprising:
    a top piece, a middle piece, and a bottom piece,
        wherein said top piece comprises a first carrier material comprising an immobilized OP/C Detecting Enzyme;
    wherein said middle piece comprises a second carrier material and an ampoule comprising a buffer; and
        wherein a first substrate, a second enzyme, a second substrate, and a pH Sensitive Dye are localized in the top piece, the middle piece, or the ampoule; and
        wherein when the middle piece is turned relative to either the top piece or the bottom piece, the ampoule is capable of being cracked to release the buffer to contact the first carrier material and the second carrier material causing:
            (i) an enzymatic conversion of the first substrate by the immobilized OP-Detecting Enzyme to produce an acidic reaction product; and
            (ii) an enzymatic conversion of the second substrate by the second enzyme to produce a basic reaction product.

2. The device of claim 1, wherein the immobilized OP/C Detecting Enzyme is:
    a) a hydrolase;
    b) a lipase, a phosphatase, an amylase, a cellulase, a protease, a peptidase, a urease or a deaminase;
    c) a carboxylesterase (CES), acetylcholinesterase (AChE), butyrylcholinesterase (BChE), organophosphorus hydrolase or organophosphorus acid anhydrolase;
    d) CES1 or CES2;
    e) Wild type carboxylesterase αE7 from the Australian blow fly *Lucilia cuprina* (LcαE7);
    f) mutant form of LcαE7$^{G137D}$
    g) LcαE7 mutants E183, K275, E78 and/or E292
    h) Wild type AChE;
    i) Mutant AChE;
    j) HuAChE containing two mutations in the acyl pocket residues (F295L, F297V);
    k) Carboxylesterase (Cqestβ2) from the *Culex quinquefasciatus* mosquito
    l) O95000, O95001, P06276, P32751, O5UR02, P32749, P32750, O62760, P81908, O03311, O62761, P32752, P21927, P32753, A1CFK9, A0A075TXZ3, D4AV38, O4F883, O31452, O8VCT4, P16303, O91WU0, O9SMM9, O9LVB8, O9SX78, O9FX92, O9FG13, O9FX93, O9LK21, O9SMN0, O8LED9, O9LFR7, O9LT10, O64641, O0ZPV7, O9LMA7, O9FX94, O9SX25, O9ZO91, O64640, B3PI89, O21FY5, C5BMZ8, O5NUF3, O5NUF4, P81098, P23141, O46421, O64419, O5RCL7, P81429, O47M62, O64573, P25727, O81034, O00748, O3T930, O16170, O64176, O63108, P16854, O6UWW8, O51758, P10094, O16173, O07085, O6NT32, O5GRG2, O53547, O16171, P47982, O08662, O33407, P81012, P81011, O9WYH1, A4KX74, P35501, O0E588, P18167, O06174, P23953, P10959, O04456, O04457, O63880, O8VCU1, O8VCC2, O29550, P12337, P86325, O6AW47, O16168, P21370, O6AW46, P14943, O16172, P25726, O16169, P25725, P10095, O63010, B2DOJ5, P08171, O6B6R8, P35502, O880S0, O05487, O32232, O9HZY8, P9WK87, O06350, L0TC47, P9WK86, P96688, O867X3, P04058, O867X2, P38433, P21836, P56161, P07140, O62763, P36196, O92081, O869C3, O27459, O42275, P07692, P23795, O86GC8, O27677, P37136, O86GC9, W4VSJ0, O9DDE3, P22303, O7LZG1, O9NDG8, O29499, or O92035; or
    m) an OP/C Detecting Enzyme Variant having at least 70%, at least 75%, at least 80%, at least 85%, at least 90, at least 91%, at least 92%, at least 93%, at least 94%, at least 95%, at least 96%, at least 97%, at least 98%, or at least 99% identity to the OP/C Detecting Enzyme amino acid sequence of (a)-(k), wherein the OP/C Detecting Enzyme Variant:
        (1) retains the ability to convert the first substrate into acetic acid; and
        (2) maintains that ability to be inhibited by an OP.

3. The device of claim 1, wherein the immobilized OP/C Detecting Enzyme:

(a) can detect at least 10 ug, at least 20 ug, at least 30 ug, at least 40 ug, at least 50 ug, at least 60 ug, at least 70 ug, at least 80 ug, at least 90 ug or at least 100 ug of an OP/C compound;

(b) can detect between 10-100 ug, between 20-100 ug, between 30-100 ug, between 40-100 ug, between 50-100 ug, between 60-100 ug, between 70-100 ug, between 80-100 ug, between 90-100 ug of an OP/C compound;

(c) comprises an inhibition rate constant $k_i$ of at least $10^3$ $M^{-1} \cdot min^{-1}$ to $10^8 M^{-1} \cdot min^{-1}$, at least $10^4 M^{-1} \cdot min^{-1}$ to $10^8 M^{-1} \cdot min^{-1}$, at least $10^5 M^{-1} \cdot min^{-1}$ to $10^8 M^{-1} \cdot min^{-1}$, at least $10^6 M^{-1} \cdot min^{-1}$ to $10^8 M^{-1} \cdot min^{-1}$, or at least $10^7 M^{-1} \cdot min^{-1}$ to $10^8 M^{-1} \cdot min^{-1}$; and/or (d) comprises an inhibition rate constant $k_i$ of $10^3$-$10^5$ $M^{-1} \cdot min^{-1}$, $k_i$ of $10^4$-$10^5$ $M^{-1} \cdot min^{-1}$, $10^5$-$10^6$ $M^{-1} \cdot min^{-1}$, $10^6$ $M^{-1} \cdot min^{-1}$ to $10^7$ $M^{-1} \cdot min^{-1}$, or $10^6$ $M^{-1} \cdot min^{-1}$ to $10^8$ $M^{-1} \cdot min^{-1}$.

4. The device of claim 1, wherein the first carrier material is comprised of:

(a) natural polymers selected from cellulose, hemicellulose, pectin, chitin, silk, lignin, starch, polypeptides, collagens, keratins, polysaccharides, nucleic acids, and rubbers; or (b) derivatives of natural polymers selected from methylation, carboxylation, amidation, sulfation, hydroxylation, condensation, iodination, reduction, oxidation, esterification, alkylation, and halogenation; and/or (c) synthetic polymers and copolymers selected from polyurethanes, thermoplastic polyurethanes, silicones, polyamides, polystyrenes, bakelite, polyethylene, polypropylene, polyvinyl chloride, Polytetrafluoroethylene, Polychloroprene, and polyimides.

5. The device of claim 1 wherein the first carrier material is a sponge.

6. The device of claim 1 wherein the first carrier material is composed of polyurethane.

7. The device of claim 1, wherein the first substrate is selected from acetylcholine, acetylthiocholine, butyrylcholine, butyrylthiocholine, 4-nitrophenyl acetate, 4-nitrophenyl propionate, 4-nitrophenyl butyrate, 4-nitrophenyl valerate, 4-nitrophenyl dimethylacetate, 4-nitrophenyl trimethylacetate, 4-nitrophenyl 4-guanidinobenzoate, or 6-nitrocoumarin.

8. The device of claim 1, wherein the second enzyme and second substrate is selected from urease, allophanate hydrolase, urea amidolyase, biuret amidohydrolase, transketolase, adenosine deaminase, adenine deaminase, guanosine deaminase, guanine deaminase (Cypin), or cytidine deaminase.

9. The device of claim 1 wherein the second enzyme is urease and the second substrate is urea.

10. The device of claim 1 wherein the basic reaction product is ammonia.

11. The device of claim 1, wherein the pH Sensitive Dye is selected from nitrazine, phenol red, chlorophenol red, bromocresol green, cresol red, bromomethyl blue, or bromocresol purple.

12. The device of claim 1 wherein the device further comprises an Oxidizer that converts an inactive OP/C compound to an active OP/C compound.

13. The device of claim 12, wherein the Oxidizer is a P450 enzyme in the presence of the cofactor NADPH.

14. The device of claim 13, wherein the P450 enzyme is a wildtype or a triple mutant of CYP1A2 (P450 BM-3 (CYP102-A1).

15. The device of claim 1, wherein:

a) the first carrier material further comprises the pH Sensitive Dye, the second enzyme and/or the Oxidizer;

b) the ampoule further comprises the pH Sensitive Dye; and/or c) the second carrier material comprises the pH Sensitive Dye, the first substrate, the second substrate, and/or the Oxidizer.

16. The device of claim 1, wherein the second carrier material is selected from:

(a) natural polymers selected from cellulose, hemicellulose, pectin, chitin, silk, lignin, starch, polypeptides, collagens, keratins, polysaccharides, nucleic acids, and rubbers; or (b) derivatives of natural polymers selected from methylation, carboxylation, amidation, sulfation, hydroxylation, condensation, iodination, reduction, oxidation, esterification, alkylation, and halogenation; and/or (c) synthetic polymers and copolymers selected from polyurethanes, thermoplastic polyurethanes, silicones, polyamides, polystyrenes, bakelite, polyethylene, polypropylene, polyvinyl chloride, Polytetrafluoroethylene, Polychloroprene, and polyimides.

17. The device of claim 1, wherein the pH Sensitive Dye, the first substrate, the second substrate, and/or the Oxidizer are lyophilized as a microtablet.

18. The device of claim 1, wherein the top piece and the middle piece are connected.

19. The device of claim 1, wherein the ampoule extends into the bottom piece.

20. The device of claim 19, wherein the middle piece contains one or more holes to permit flow of released contents of the ampoule between the bottom piece and the middle piece.

21. The device of claim 1, wherein the device further comprises a lid.

22. The device of claim 21, wherein the lid is transparent and/or comprises a window.

23. The device of claim 1, wherein the device comprises at least one O-ring.

24. The device of claim 1, wherein the device is operably associated with a smart phone.

25. The device of claim 1 wherein the immobilized OP/C Detecting Enzyme is produced by a plant cell, a mammalian cell, or a bacterial cell.

\* \* \* \* \*

SEQUENCE LISTING

```
<160> NUMBER OF SEQ ID NOS: 6

<210> SEQ ID NO 1
<211> LENGTH: 614
<212> TYPE: PRT
<213> ORGANISM: homo sapiens

<400> SEQUENCE: 1

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asn Ala Thr Thr Phe
                85                  90                  95

Gln Ser Val Cys Tyr Gln Tyr Val Asp Thr Leu Tyr Pro Gly Phe Glu
                100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
            195                 200                 205
```

```
Leu Ala Leu Gln Trp Val Gln Glu Asn Val Ala Ala Phe Gly Gly Asp
    210             215             220
```

```
Pro Thr Ser Val Thr Leu Phe Gly Glu Ser Ala Gly Ala Ala Ser Val
225             230             235             240
```

```
Gly Met His Leu Leu Ser Pro Pro Ser Arg Gly Leu Phe His Arg Ala
            245             250             255
```

```
Val Leu Gln Ser Gly Ala Pro Asn Gly Pro Trp Ala Thr Val Gly Met
            260             265             270
```

```
Gly Glu Ala Arg Arg Arg Ala Thr Gln Leu Ala His Leu Val Gly Cys
            275             280             285
```

```
Pro Pro Gly Gly Thr Gly Gly Asn Asp Thr Glu Leu Val Ala Cys Leu
    290             295             300
```

```
Arg Thr Arg Pro Ala Gln Val Leu Val Asn His Glu Trp His Val Leu
305             310             315             320
```

```
Pro Gln Glu Ser Val Phe Arg Phe Ser Phe Val Pro Val Val Asp Gly
            325             330             335
```

```
Asp Phe Leu Ser Asp Thr Pro Glu Ala Leu Ile Asn Ala Gly Asp Phe
            340             345             350
```

```
His Gly Leu Gln Val Leu Val Gly Val Val Lys Asp Glu Gly Ser Tyr
            355             360             365
```

```
Phe Leu Val Tyr Gly Ala Pro Gly Phe Ser Lys Asp Asn Glu Ser Leu
    370             375             380
```

```
Ile Ser Arg Ala Glu Phe Leu Ala Gly Val Arg Val Gly Val Pro Gln
385             390             395             400
```

```
Val Ser Asp Leu Ala Ala Glu Ala Val Val Leu His Tyr Thr Asp Trp
            405             410             415
```

```
Leu His Pro Glu Asp Pro Ala Arg Leu Arg Glu Ala Leu Ser Asp Val
            420             425             430
```

```
Val Gly Asp His Asn Val Val Cys Pro Val Ala Gln Leu Ala Gly Arg
            435             440             445
```

```
Leu Ala Ala Gln Gly Ala Arg Val Tyr Ala Tyr Val Phe Glu His Arg
    450             455             460
```

```
Ala Ser Thr Leu Ser Trp Pro Leu Trp Met Gly Val Pro His Gly Tyr
465             470             475             480
```

```
Glu Ile Glu Phe Ile Phe Gly Ile Pro Leu Asp Pro Ser Arg Asn Tyr
            485             490             495
```

```
Thr Ala Glu Glu Lys Ile Phe Ala Gln Arg Leu Met Arg Tyr Trp Ala
            500             505             510
```

```
Asn Phe Ala Arg Thr Gly Asp Pro Asn Glu Pro Arg Asp Pro Lys Ala
            515             520             525
```

```
Pro Gln Trp Pro Pro Tyr Thr Ala Gly Ala Gln Gln Tyr Val Ser Leu
    530             535             540
```

```
Asp Leu Arg Pro Leu Glu Val Arg Arg Gly Leu Arg Ala Gln Ala Cys
545             550             555             560
```

```
Ala Phe Trp Asn Arg Phe Leu Pro Lys Leu Leu Asn Ala Thr Asp Thr
            565             570             575
```

```
Leu Asp Glu Ala Glu Arg Gln Trp Lys Ala Glu Phe His Arg Trp Ser
            580             585             590
```

```
Ser Tyr Met Val His Trp Lys Asn Gln Phe Asp His Tyr Ser Lys Gln
            595             600             605
```

```
Asp Arg Cys Ser Asp Leu
    610
```

-continued

```
<210> SEQ ID NO 2
<211> LENGTH: 520
<212> TYPE: PRT
<213> ORGANISM: Macaca

<400> SEQUENCE: 2

Met Leu Leu Leu Ser Arg Ala Cys Ala Thr Ser Met Trp Ile Pro Phe
1               5                   10                  15

Thr Leu Val Ser Arg Glu Leu Arg Cys Gly Thr Leu Thr Glu Ser Cys
            20                  25                  30

Leu Arg Ile Ala Cys Thr Leu Met Cys Gly Pro Arg Pro Thr Ser Pro
        35                  40                  45

Thr Pro Val Leu Val Trp Ile Tyr Gly Gly Gly Phe Tyr Ser Gly Ala
    50                  55                  60

Ser Ser Leu Asp Val Tyr Asp Gly Arg Phe Leu Val Gln Ala Glu Arg
65                  70                  75                  80

Thr Val Leu Val Ser Met Asn Tyr Arg Val Gly Ala Phe Gly Phe Leu
                85                  90                  95

Ala Leu Pro Gly Ser Arg Glu Ala Pro Gly Asn Val Gly Leu Leu Asp
            100                 105                 110

Gln Arg Leu Ala Leu Gln Trp Val Gln Glu Asn Val Ala Ala Phe Gly
        115                 120                 125

Gly Asp Pro Thr Ser Val Thr Leu Phe Gly Glu Ser Ala Gly Ala Ala
        130                 135                 140

Ser Val Gly Met His Leu Leu Ser Pro Pro Ser Arg Gly Leu Phe His
145                 150                 155                 160

Arg Ala Val Leu Gln Ser Gly Ala Pro Asn Gly Pro Trp Ala Thr Val
                165                 170                 175

Gly Met Gly Glu Ala Arg Arg Arg Ala Thr Gln Leu Ala His Leu Val
            180                 185                 190

Gly Cys Pro Pro Gly Gly Thr Gly Gly Asn Asp Thr Glu Leu Val Ala
            195                 200                 205

Cys Leu Arg Thr Arg Pro Ala Gln Val Leu Val Asn Asn Glu Trp His
        210                 215                 220

Val Leu Pro Gln Glu Ser Val Phe Arg Phe Ser Phe Val Pro Val Val
225                 230                 235                 240

Asp Gly Asp Phe Leu Ser Asp Thr Pro Glu Ala Leu Ile Asn Ala Gly
                245                 250                 255

Asp Phe His Gly Leu Gln Val Leu Val Gly Val Val Lys Asp Glu Gly
            260                 265                 270

Ser Tyr Phe Leu Val Tyr Gly Ala Pro Gly Phe Ser Lys Asp Asn Glu
            275                 280                 285

Ser Leu Ile Ser Arg Ala Glu Phe Leu Ala Gly Val Arg Val Gly Val
        290                 295                 300

Pro Gln Val Ser Asp Leu Ala Ala Glu Ala Val Val Leu His Tyr Thr
305                 310                 315                 320

Asp Trp Leu His Pro Glu Asp Pro Ala Arg Leu Arg Glu Ala Leu Ser
                325                 330                 335

Asp Val Val Gly Asp His Asn Val Val Cys Pro Val Ala Gln Leu Ala
            340                 345                 350

Gly Arg Leu Ala Ala Gln Gly Ala Arg Val Tyr Ala Tyr Val Phe Glu
        355                 360                 365

His Arg Ala Ser Thr Leu Ser Trp Pro Leu Trp Met Gly Val Pro His
    370                 375                 380
```

-continued

```
Gly Tyr Glu Ile Glu Phe Ile Phe Gly Ile Pro Leu Asp Pro Ser Arg
385                 390                 395                 400

Asn Tyr Thr Thr Glu Glu Lys Ile Phe Ala Gln Arg Leu Met Arg Tyr
                405                 410                 415

Trp Ala Asn Phe Ala Arg Thr Gly Asp Pro Asn Glu Pro Arg Asp Pro
            420                 425                 430

Lys Ala Pro Gln Trp Pro Pro Tyr Thr Ala Gly Ala Gln Gln Tyr Val
        435                 440                 445

Ser Leu Asp Leu Arg Pro Leu Glu Val Arg Arg Gly Leu Arg Ala Gln
    450                 455                 460

Ala Cys Ala Phe Trp Asn Arg Phe Leu Pro Lys Leu Leu Ser Ala Thr
465                 470                 475                 480

Asp Thr Leu Asp Glu Ala Glu Arg Gln Trp Lys Ala Glu Phe His Arg
                485                 490                 495

Trp Ser Ser Tyr Met Val His Trp Lys Asn Gln Phe Asp His Tyr Ser
            500                 505                 510

Lys Gln Asp Arg Cys Ser Asp Leu
        515                 520

<210> SEQ ID NO 3
<211> LENGTH: 602
<212> TYPE: PRT
<213> ORGANISM: Homo sapiens

<400> SEQUENCE: 3

Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
            85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
    130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
        210                 215                 220

Glu Ser Ala Gly Ala Ala Ser Val Ser Leu His Leu Leu Ser Pro Gly
```

-continued

```
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
                260                 265                 270

Asn Leu Ala Lys Leu Thr Gly Cys Ser Arg Glu Asn Glu Thr Glu Ile
                275                 280                 285

Ile Lys Cys Leu Arg Asn Lys Asp Pro Gln Glu Ile Leu Leu Asn Glu
                290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
                340                 345                 350

Glu Gly Thr Ala Phe Leu Val Tyr Gly Ala Pro Gly Phe Ser Lys Asp
                355                 360                 365

Asn Asn Ser Ile Ile Thr Arg Lys Glu Phe Gln Glu Gly Leu Lys Ile
                370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
                435                 440                 445

Phe Glu His Arg Ser Ser Lys Leu Pro Trp Pro Glu Trp Met Gly Val
                450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
                500                 505                 510

Asn Asn Ser Thr Ser Trp Pro Val Phe Lys Ser Thr Glu Gln Lys Tyr
                515                 520                 525

Leu Thr Leu Asn Thr Glu Ser Thr Arg Ile Met Thr Lys Leu Arg Ala
                530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
                595                 600

<210> SEQ ID NO 4
<211> LENGTH: 602
<212> TYPE: PRT
<213> ORGANISM: Macaca

<400> SEQUENCE: 4
```

```
Met Asp Ser Lys Val Thr Ile Ile Cys Ile Arg Leu Leu Phe Trp Phe
1               5                   10                  15

Leu Leu Leu Cys Met Leu Ile Gly Lys Ser His Thr Glu Asp Asp Ile
            20                  25                  30

Val Ile Ala Thr Lys Asn Gly Lys Val Arg Gly Met Asn Leu Thr Val
            35                  40                  45

Leu Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Tyr Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Met Ile Trp Ile Tyr Gly Gly
        130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
            165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
        210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Ser Asn
                245                 250                 255

Ala Pro Trp Ala Val Thr Ser Leu Tyr Glu Ala Arg Asn Arg Thr Leu
            260                 265                 270

Thr Leu Ala Lys Leu Thr Gly Cys Ser Arg Asp Asn Glu Thr Glu Ile
        275                 280                 285

Val Lys Cys Leu Arg Asn Lys Asp Pro His Glu Ile Leu Leu Asn Glu
    290                 295                 300

Ala Phe Val Val Pro Tyr Gly Thr Leu Leu Ser Val Asn Phe Gly Pro
305                 310                 315                 320

Thr Met Asp Gly Asp Phe Leu Thr Glu Met Pro Asp Ile Leu Leu Glu
            325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
            355                 360                 365

Asn Asp Ser Ile Ile Thr Arg Asn Glu Phe Gln Glu Gly Leu Lys Ile
        370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Asp Asp Val Val Gly Asp Tyr Asn Ile Ile Cys Pro Ala Leu Glu
```

-continued

```
                420             425             430

Phe Thr Lys Lys Phe Ser Glu Trp Gly Asn Asn Ala Phe Phe Tyr Tyr
        435             440             445

Phe Glu His Arg Ser Ser Lys Leu Pro Trp Pro Glu Trp Met Gly Val
    450             455             460

Met His Gly Tyr Glu Ile Glu Phe Val Phe Gly Leu Pro Leu Glu Arg
465             470             475             480

Arg Val Asn Tyr Thr Lys Ala Glu Glu Ile Leu Ser Arg Ser Ile Val
                485             490             495

Lys Arg Trp Ala Asn Phe Ala Lys Tyr Gly Asn Pro Asn Gly Thr His
            500             505             510

Asn Asn Ser Thr Lys Trp Pro Val Phe Lys Ser Thr Glu Gln Lys Tyr
            515             520             525

Leu Thr Leu Asn Thr Glu Ser Ser Arg Ile Leu Thr Lys Leu Arg Ala
        530             535             540

Gln Gln Cys Arg Phe Trp Thr Ser Phe Phe Pro Lys Val Leu Glu Met
545             550             555             560

Thr Gly Asn Ile Asp Glu Ala Glu Trp Glu Trp Lys Ala Gly Phe His
            565             570             575

Arg Trp Ser Asn Tyr Met Met Asp Trp Lys Asn Gln Phe Asn Asp Tyr
            580             585             590

Thr Ser Lys Lys Glu Ser Cys Val Gly Leu
            595             600

<210> SEQ ID NO 5
<211> LENGTH: 566
<212> TYPE: PRT
<213> ORGANISM: Homo sapiens

<400> SEQUENCE: 5

Met Trp Leu Pro Ala Leu Val Leu Ala Thr Leu Ala Ala Ser Ala Ala
1               5               10              15

Trp Gly His Pro Ser Ser Pro Pro Val Val Asp Thr Val His Gly Lys
            20              25              30

Val Leu Gly Lys Phe Val Ser Leu Glu Gly Phe Ala Gln Pro Val Ala
        35              40              45

Ile Phe Leu Gly Ile Pro Phe Ala Lys Pro Pro Leu Gly Pro Leu Arg
    50              55              60

Phe Thr Pro Pro Gln Pro Ala Glu Pro Trp Ser Phe Val Lys Asn Ala
65              70              75              80

Thr Ser Tyr Pro Pro Met Cys Thr Gln Asp Pro Lys Ala Gly Gln Leu
            85              90              95

Leu Ser Glu Leu Phe Thr Asn Arg Lys Glu Asn Ile Pro Leu Lys Leu
            100             105             110

Ser Glu Asp Cys Leu Tyr Leu Asn Ile Tyr Thr Pro Ala Asp Leu Thr
            115             120             125

Lys Lys Asn Arg Leu Pro Val Met Val Trp Ile His Gly Gly Gly Leu
        130             135             140

Met Val Gly Ala Ala Ser Thr Tyr Asp Gly Leu Ala Leu Ala Ala His
145             150             155             160

Glu Asn Val Val Val Val Thr Ile Gln Tyr Arg Leu Gly Ile Trp Gly
                165             170             175

Phe Phe Ser Thr Gly Asp Glu His Ser Arg Gly Asn Trp Gly His Leu
            180             185             190
```

```
Asp Gln Val Ala Ala Leu Arg Trp Val Gln Asp Asn Ile Ala Ser Phe
        195                 200                 205

Gly Gly Asn Pro Gly Ser Val Thr Ile Phe Gly Glu Ser Ala Gly Gly
        210                 215                 220

Glu Ser Val Ser Val Leu Val Leu Ser Pro Leu Ala Lys Asn Leu Phe
225                 230                 235                 240

His Arg Ala Ile Ser Glu Ser Gly Val Ala Leu Thr Ser Val Leu Val
                245                 250                 255

Lys Lys Gly Asp Val Lys Pro Leu Ala Glu Gln Ile Ala Ile Thr Ala
                260                 265                 270

Gly Cys Lys Thr Thr Thr Ser Ala Val Met Val His Cys Leu Arg Gln
                275                 280                 285

Lys Thr Glu Glu Glu Leu Leu Glu Thr Thr Leu Lys Met Lys Phe Leu
        290                 295                 300

Ser Leu Asp Leu Gln Gly Asp Pro Arg Glu Ser Gln Pro Leu Leu Gly
305                 310                 315                 320

Thr Val Ile Asp Gly Met Leu Leu Leu Lys Thr Pro Glu Glu Leu Gln
                325                 330                 335

Ala Glu Arg Asn Phe His Thr Val Pro Tyr Met Val Gly Ile Asn Lys
                340                 345                 350

Gln Glu Phe Gly Trp Leu Ile Pro Met Leu Met Ser Tyr Pro Leu Ser
        355                 360                 365

Glu Gly Gln Leu Asp Gln Lys Thr Ala Met Ser Leu Leu Trp Lys Ser
        370                 375                 380

Tyr Pro Leu Val Cys Ile Ala Lys Glu Leu Ile Pro Glu Ala Thr Glu
385                 390                 395                 400

Lys Tyr Leu Gly Gly Thr Asp Asp Thr Val Lys Lys Lys Asp Leu Phe
                405                 410                 415

Leu Asp Leu Ile Ala Asp Val Met Phe Gly Val Pro Ser Val Ile Val
                420                 425                 430

Ala Arg Asn His Arg Asp Ala Gly Ala Pro Thr Tyr Met Tyr Glu Phe
                435                 440                 445

Gln Tyr Arg Pro Ser Phe Ser Ser Asp Met Lys Pro Lys Thr Val Ile
        450                 455                 460

Gly Asp His Gly Asp Glu Leu Phe Ser Val Phe Gly Ala Pro Phe Leu
465                 470                 475                 480

Lys Glu Gly Ala Ser Glu Glu Glu Ile Arg Leu Ser Lys Met Val Met
                485                 490                 495

Lys Phe Trp Ala Asn Phe Ala Arg Asn Gly Asn Pro Asn Gly Glu Gly
                500                 505                 510

Leu Pro His Trp Pro Glu Tyr Asn Gln Lys Glu Gly Tyr Leu Gln Ile
        515                 520                 525

Gly Ala Asn Thr Gln Ala Ala Gln Lys Leu Lys Asp Lys Glu Val Ala
        530                 535                 540

Phe Trp Thr Asn Leu Phe Ala Lys Lys Ala Val Glu Lys Pro Pro Gln
545                 550                 555                 560

Thr Glu His Ile Glu Leu
                565

<210> SEQ ID NO 6
<211> LENGTH: 550
<212> TYPE: PRT
<213> ORGANISM: Homo sapiens

<400> SEQUENCE: 6
```

```
Met Ser Ala Val Ala Cys Gly Leu Leu Leu Leu Val Arg Gly Gln
1               5                   10                  15

Gly Gln Asp Ser Ala Ser Pro Ile Arg Thr Thr His Thr Gly Gln Val
            20                  25                  30

Leu Gly Ser Leu Val His Val Lys Gly Ala Asn Ala Gly Val Gln Thr
            35                  40                  45

Phe Leu Gly Ile Pro Phe Ala Lys Pro Pro Leu Gly Pro Leu Arg Phe
    50                  55                  60

Ala Pro Pro Glu Pro Pro Glu Ser Trp Ser Gly Val Arg Asp Gly Thr
65                  70                  75                  80

Thr His Pro Ala Met Cys Leu Gln Asp Leu Thr Ala Val Glu Ser Glu
                85                  90                  95

Phe Leu Ser Gln Phe Asn Met Thr Phe Pro Ser Asp Ser Met Ser Glu
            100                 105                 110

Asp Cys Leu Tyr Leu Ser Ile Tyr Thr Pro Ala His Ser His Glu Gly
            115                 120                 125

Ser Asn Leu Pro Val Met Val Trp Ile His Gly Gly Ala Leu Val Phe
    130                 135                 140

Gly Met Ala Ser Leu Tyr Asp Gly Ser Met Leu Ala Ala Leu Glu Asn
145                 150                 155                 160

Val Val Val Val Ile Ile Gln Tyr Arg Leu Gly Val Leu Gly Phe Phe
                165                 170                 175

Ser Thr Gly Asp Lys His Ala Thr Gly Asn Trp Gly Tyr Leu Asp Gln
            180                 185                 190

Val Ala Ala Leu Arg Trp Val Gln Gln Asn Ile Ala His Phe Gly Gly
            195                 200                 205

Asn Pro Asp Arg Val Thr Ile Phe Gly Glu Ser Ala Gly Gly Thr Ser
    210                 215                 220

Val Ser Ser Leu Val Val Ser Pro Ile Ser Gln Gly Leu Phe His Gly
225                 230                 235                 240

Ala Ile Met Glu Ser Gly Val Ala Leu Leu Pro Gly Leu Ile Ala Ser
                245                 250                 255

Ser Ala Asp Val Ile Ser Thr Val Val Ala Asn Leu Ser Ala Cys Asp
            260                 265                 270

Gln Val Asp Ser Glu Ala Leu Val Gly Cys Leu Arg Gly Lys Ser Lys
            275                 280                 285

Glu Glu Ile Leu Ala Ile Asn Lys Pro Phe Lys Met Ile Pro Gly Val
    290                 295                 300

Val Asp Gly Val Phe Leu Pro Arg His Pro Gln Glu Leu Leu Ala Ser
305                 310                 315                 320

Ala Asp Phe Gln Pro Val Pro Ser Ile Val Gly Val Asn Asn Asn Glu
                325                 330                 335

Phe Gly Trp Leu Ile Pro Lys Val Met Arg Ile Tyr Asp Thr Gln Lys
            340                 345                 350

Glu Met Asp Arg Glu Ala Ser Gln Ala Ala Leu Gln Lys Met Leu Thr
            355                 360                 365

Leu Leu Met Leu Pro Pro Thr Phe Gly Asp Leu Leu Arg Glu Glu Tyr
    370                 375                 380

Ile Gly Asp Asn Gly Asp Pro Gln Thr Leu Gln Ala Gln Phe Gln Glu
385                 390                 395                 400

Met Met Ala Asp Ser Met Phe Val Ile Pro Ala Leu Gln Val Ala His
                405                 410                 415
```

```
Phe Gln Cys Ser Arg Ala Pro Val Tyr Phe Tyr Glu Phe Gln His Gln
            420             425                 430

Pro Ser Trp Leu Lys Asn Ile Arg Pro Pro His Met Lys Ala Asp His
        435             440                 445

Gly Asp Glu Leu Pro Phe Val Phe Arg Ser Phe Phe Gly Gly Asn Tyr
    450             455             460

Ile Lys Phe Thr Glu Glu Glu Glu Gln Leu Ser Arg Lys Met Met Lys
465             470                 475                 480

Tyr Trp Ala Asn Phe Ala Arg Asn Gly Asn Pro Asn Gly Glu Gly Leu
            485             490                 495

Pro His Trp Pro Leu Phe Asp Gln Glu Glu Gln Tyr Leu Gln Leu Asn
        500             505             510

Leu Gln Pro Ala Val Gly Arg Ala Leu Lys Ala His Arg Leu Gln Phe
        515             520                 525

Trp Lys Lys Ala Leu Pro Gln Lys Ile Gln Glu Leu Glu Glu Pro Glu
        530             535                 540

Glu Arg His Thr Glu Leu
545             550
```